US006187210B1

(12) United States Patent
Lebouitz et al.

(10) Patent No.: US 6,187,210 B1
(45) Date of Patent: Feb. 13, 2001

(54) EPIDERMAL ABRASION DEVICE WITH ISOTROPICALLY ETCHED TIPS, AND METHOD OF FABRICATING SUCH A DEVICE

(75) Inventors: Kyle S. Lebouitz, Albany; Albert P. Pisano, Livermore, both of CA (US)

(73) Assignee: The Regents of the University of California, Oakland, CA (US)

( * ) Notice: Under 35 U.S.C. 154(b), the term of this patent shall be extended for 0 days.

(21) Appl. No.: 09/106,991

(22) Filed: Jun. 29, 1998

Related U.S. Application Data

(63) Continuation-in-part of application No. 08/884,867, filed on Jun. 30, 1997, now Pat. No. 5,928,207.

(51) Int. Cl.$^7$ .............................. H01L 21/00; C23F 1/00; A61M 5/32

(52) U.S. Cl. .................. 216/11; 216/2; 216/99; 438/52; 438/745; 604/187

(58) Field of Search .................. 604/187; 216/2, 216/11, 39, 56, 99; 438/52, 53, 745, 753

(56) References Cited

U.S. PATENT DOCUMENTS

| | | | |
|---|---|---|---|
| 5,342,397 | 8/1994 | Guido | 606/222 |
| 5,386,110 * | 1/1995 | Toda | 250/216 |
| 5,879,326 | 3/1999 | Godshall et al. | 604/506 |

OTHER PUBLICATIONS

Henry, et al., "Micofabricated Microneedles: A Novel Approach to Transdermal Drug Delivery", *Journal of Pharmaceutical Sciences*, vol. 87, No. 8, pp. 992–925, 1998.
McAllister, et al., "Three–Dimensional Hollow Microneedle and Microtube Arrays" *Transducers '99*, pp. 1098–1101, Sendai, Japan, 1999.
McAllister et al., "Microfabricated Microneedles: A Novel Approach to Transdermal Drug Delivery", Proceed. Int'l Symp. Control. Rel. Bioact. Meter., 25:30–31 (1998).
Thomas et al., "Fabrication and Some Applications of Large–Area Silicon Field Emission Arrays", *Solid–State Electronics*, 17:155–163 (1974).
Thomas et al., "Photosensitive Field Emission from Silicon Point Arrays", *Applied Physics Letter*, 21(8):384–386 (1972).
Lin et al., "Silicon Processed Microneedles", 7th International Conference on Solid–State Sensors and Actuators, Transducers '93 held in —kohama, Japan, Jun. 7–10, 1993; Dept. of Mechanical Engineering, University of California at Berkeley, CA, pp. 237–240.

* cited by examiner

*Primary Examiner*—Gregory Mills
*Assistant Examiner*—Awa C Powell
(74) *Attorney, Agent, or Firm*—William S. Galliani; Pennie & Edmonds LLP

(57) ABSTRACT

A probe includes an elongated body with a top surface, a bottom surface, a first side wall between the top surface and the bottom surface, and a second side wall between the top surface and the bottom surface. An end is defined by the bottom surface converging into a tip, an isotropically etched portion of the first side wall converging into the tip, and an isotropically etched portion of the second side wall converging into the tip. The elongated body is less than approximately 700 μm wide and less than approximately 200 μm thick. The elongated body may incorporate a fluid channel. The elongated body may be formed of silicon that is not doped with Boron. In such a configuration, integrated circuitry or a micromachined device, such as a heater or pump may also be formed on the device. A number of novel processing techniques are associate with the fabrication of the device. The device may be formed by relying solely on isotropic etching. Alternately, a combination of isotropic and anisotropic etching may be used. Unlike prior art micromachined devices, the disclosed device may be processed at relatively low temperatures below 1100° C. and without using the carcinogen ethylenediamin pyrocatechol.

11 Claims, 42 Drawing Sheets

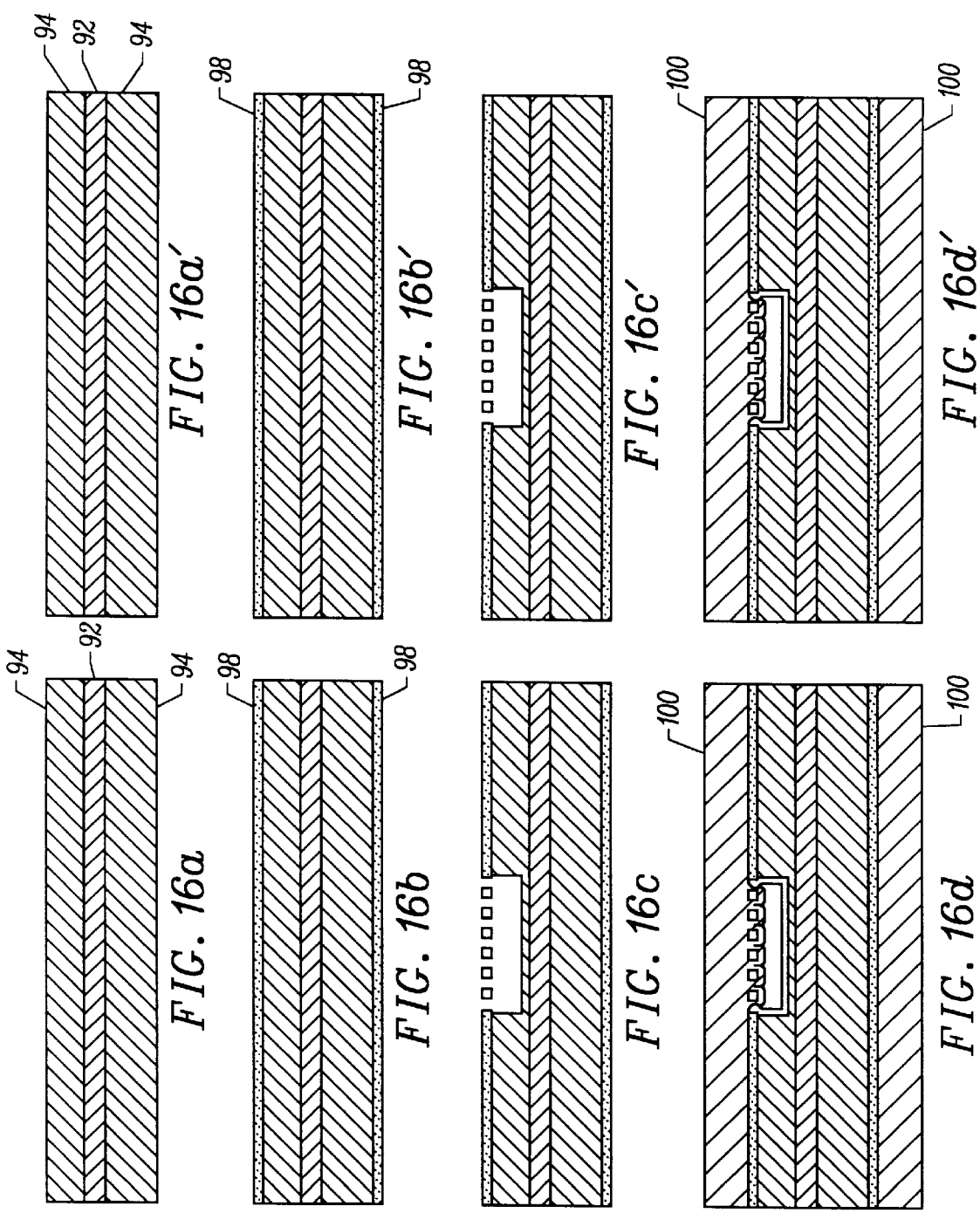

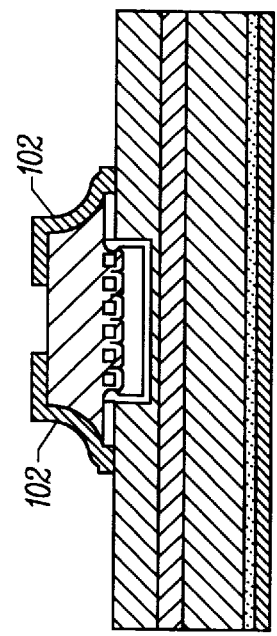 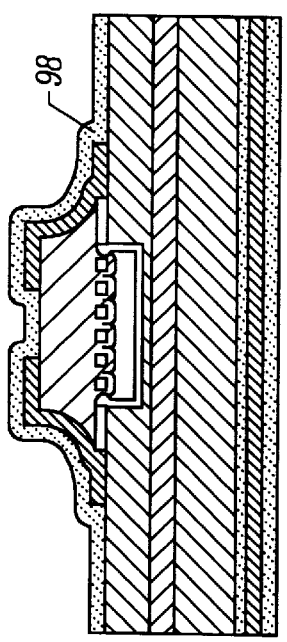 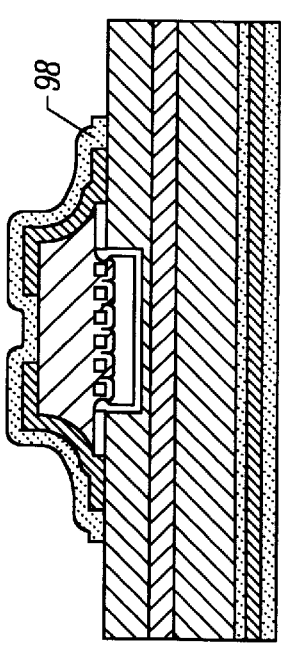
FIG. 16h  FIG. 16i  FIG. 16j
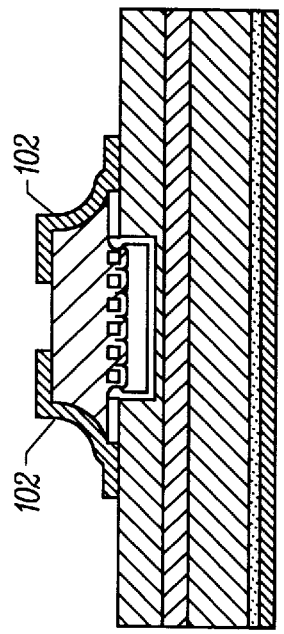 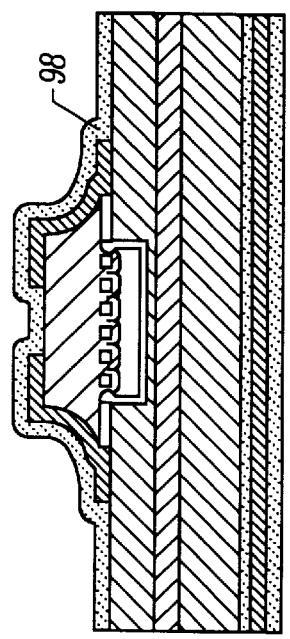 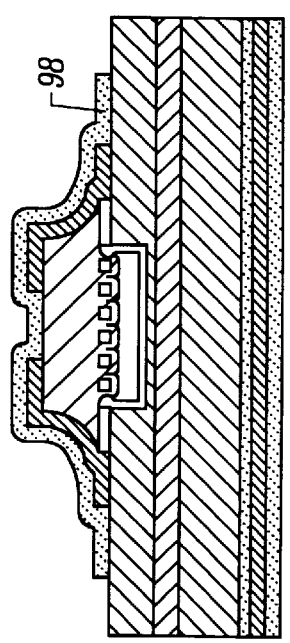
FIG. 16h'  FIG. 16i'  FIG. 16j'

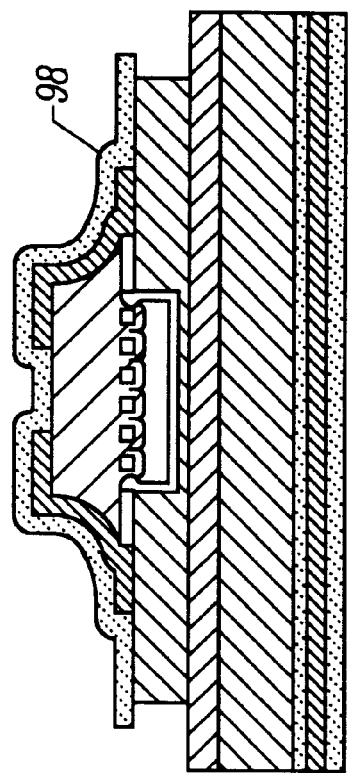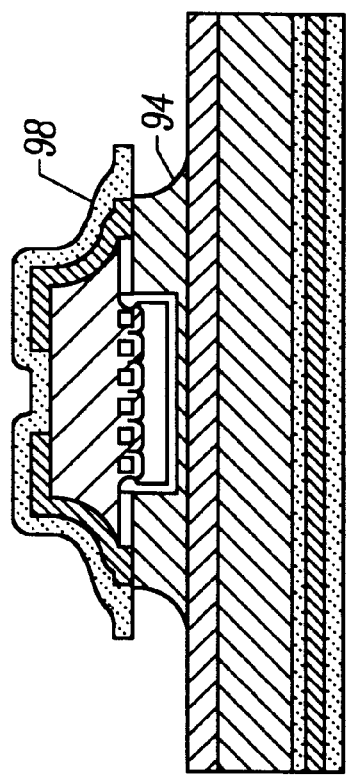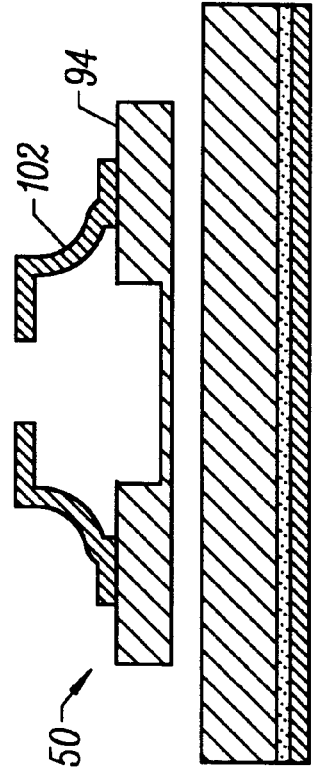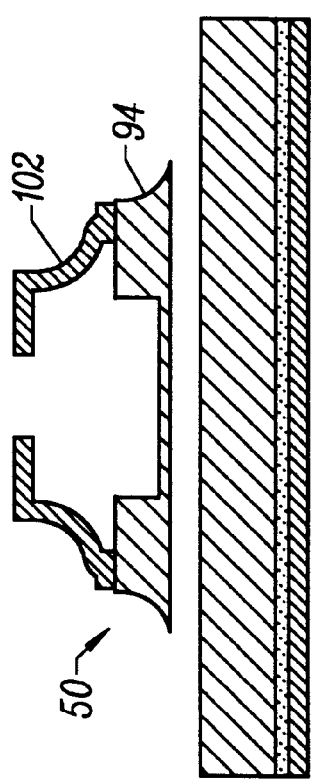
FIG. 16n'
FIG. 16o'
FIG. 16n
FIG. 16o

EPIDERMAL ABRASION DEVICE WITH ISOTROPICALLY ETCHED TIPS, AND METHOD OF FABRICATING SUCH A DEVICE

This is a continuation-in-part of application Ser. No. 08/884,867 filed Jun. 30, 1997 now U.S. Pat. No. 5,928,207.

BRIEF DESCRIPTION OF THE INVENTION

This invention relates generally to micron-scale transdermal probes, such as hypodermic needles, lancets, and blades. More particularly, this invention relates to a micron-scale transdermal probe that is formed by isotropic etching of a single crystal substrate.

BACKGROUND OF THE INVENTION

The biomedical industry seeks to replace stainless steel hypodermic injection needles with needles that have small diameters, sharper tips, and which can provide additional functionality. The advantages of smaller diameters and sharper tips are to minimize pain and tissue damage. Desirable additional functionality for a hypodermic injection needle includes the capability of providing integrated electronics for chemical concentration monitoring, cell stimulation, and the control of fluid flow, such as through an integrated valve or pump.

Integrated circuit technology and single crystal silicon wafers have been used to produce hypodermic injection needles. A "microhypodermic" injection needle or "microneedle" is described in Lin, et al., "Silicon Processed Microneedle", *Digest of Transducers '93, International Conference on Solid-State Sensors and Actuators*, pp. 237–240, June 1993. Another microneedle is described in Chen and Wise, "A Multichannel Neural Probe for Selective Chemical Delivery at the Cellular Level," *Technical Digest of the Solid-State Sensor and Actuator Workshop*, Hilton head Island, S.C., pp. 256–259, Jun. 13–16, 1994. The needles described in these references have common elements since they are both based on the process flow for a multielectrode probe. In particular, both processes rely on heavily boron doped regions to define the shape of the needle and the utilization of ethylenediamine pyrocatechol as an anisotropic etchant.

Lin, et al. describe a fluid passage that is surface micromachined and utilizes a timed etch to thin the wafer such that an approximately 50 $\mu$m thick strengthening rib of single crystal silicon remains. In contrast, Chen and Wise bulk micromachine a channel into the microneedle using an arisotropic etch and all of the single crystal silicon comprising the shaft of the needle is heavily boron doped so the timing of the anisotropic etch to form the shape of the needle is less critical.

There are a number of disadvantages associated with these prior art devices. The single crystal silicon strengthening rib in the Lin, et al. microneedle is naturally rough and is difficult to reproduce due to the tight tolerance on the timed etch. The Chen and Wise microneedle results in walls approximately 10 $\mu$m or less in thickness and the shape of the fluid channel defines the shape of the silicon comprising the structural portion of the needle. Therefore, small channels lead to thin needles and large channels lead to large needles. This is a problem when a needle with a small channel but large needle cross-section is desired. Often, large needle cross-sections are necessary, such as those 50 $\mu$m thick or greater, to obtain a stronger microneedle, but since the fluid flow rate is dependent on the cross-section of the needle, a large needle may not provide the necessary flow resistance. To establish the necessary flow resistance in a large needle cross-section, a complicated nested channel configuration must be fabricated.

The Lin, et al. and Chen and Wise microneedles share the drawback that they rely on the use of boron doping to define the shape of the needle. This requires a long (approximately 8 hours in Chen and Wise; approximately 16 hours in Lin), high temperature (approximately 1150° C.) step which is expensive. In addition, the chosen anisotropic etchant is ethylenediamine pyrocatechol, which is a strong carcinogen, making production dangerous and therefore leading to further expenses. Finally, since both of these microneedles utilize an anisotropic etchant to produce the shape of the microneedle, limitations are placed on the geometry of the needle. For the needle to be "sharpest", it is preferred for the tip of the needle to originate from a near infinitesimally small point and taper continuously, without step transitions, to the full width of the shaft of the needle. Such a geometry is not possible using the techniques described in Lin, et al. and Chen and Wise. In particular, the needles produced using those techniques have abrupt step transitions, largely attributable to the use of the anisotropic etchant.

Microneedles that do not include a channel are referred to herein as lancets. Lancets may be used to lance the epidermis so that a drop of blood can be sampled. Lancets may also be formed in configurations that allow them be used as blades or scalpals. Such devices can be used for cutting skin or eyes in a surgical context. Thus, as used herein, a transdermal probe refers to microneedles, lancets, or blades (scalpals).

It would be highly desirable to provide improved transdermal probes and processes of fabricating such probes to overcome the shortcomings associated with prior art devices.

SUMMARY OF THE INVENTION

A transdermal probe includes an elongated body with a top surface, a bottom surface, a first side wall between the top surface and the bottom surface, and a second side wall between the top surface and the bottom surface. An end is defined by the bottom surface converging into a tip, an isotropically etched portion of the first side wall converging into the tip, and an isotropically etched portion of the second side wall converging into the tip. The elongated body is less than approximately 700 $\mu$m wide and less than approximately 200 $\mu$m thick. The elongated body may incorporate a fluid channel. The elongated body may be formed of silicon that is not doped with Boron. In such a configuration, integrated circuitry or a micromachined device, such as a heater or pump may also be formed on the device. A number of novel processing techniques are associated with the fabrication of the device. The device may be formed by relying solely on isotropic etching. Alternately, a combination of isotropic and anisotropic etching may be used. Unlike prior art micromachined devices, the disclosed device may be processed at relatively low temperatures of 1100° C. or below and without using the carcinogen ethylenediamin pyrocatechol. When forming a blade, the width can be as wide as about 3 mm and the thickness can be as high as about 400 $\mu$m.

BRIEF DESCRIPTION OF THE DRAWINGS

For a better understanding of the nature and objects of the invention, reference should be made to the following detailed description taken in conjunction with the accompanying drawings, in which.

Like reference numerals refer to corresponding parts throughout the several views of the drawings.

DETAILED DESCRIPTION OF THE INVENTION

Figure 1:
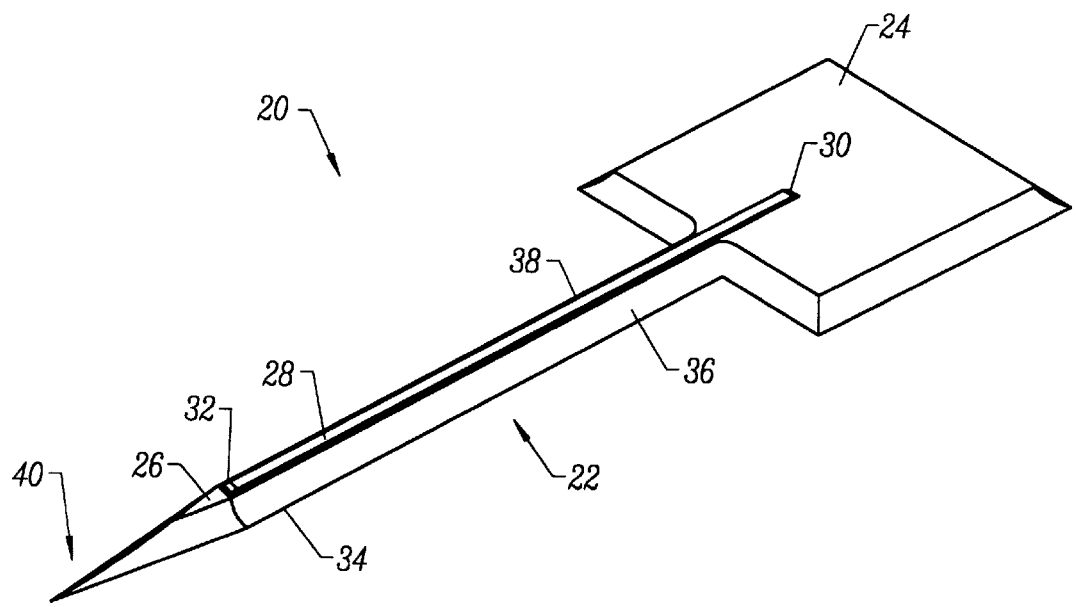
FIG. 1 is a perspective view of an isotropically etched probe in accordance with an embodiment of the invention.

FIG. 1 provides a perspective view of an isotropically etched transdermal probe 20 in accordance with an embodiment of the invention. The probe 20 includes an elongated body 22, formed of single crystal material, preferably silicon, which terminates in a shank end 24. The elongated body 22 has a top, preferably horizontal, surface 26. In the embodiment of FIG. 1, the top surface 26 has a channel cap 28, including a channel inlet/outlet port 30 and a channel outlet/inlet port 32. As will be shown below, embodiments of the probe of the invention include an integrally formed channel within the elongated body 22. The channel cap 28, which may be formed with polycrystalline silicon, covers the channel. The channel cap inlet port 30 allows fluid to enter the channel and the channel cap outlet port 32 allows fluid to exit the channel. In this configuration, the probe 20 of the invention can be used to deliver or draw fluid from a vessel, such as a living body or a drug container. Embodiments of the probe 20 do not include a channel, such embodiments are useful as lancets, which are used to lance human tissue for the purpose of drawing blood. In other embodiments of the invention, the probe may be used as a blade.

The elongated body 22 also includes a bottom, preferably horizontal, surface 34. Connected between the top surface 26 and bottom surface 34 is a first side wall 36 and a second side wall JO. In the embodiment of FIG. 1, each side wall has a curved shape attributable to an isotropic etch operation, discussed below.

Figure 2:
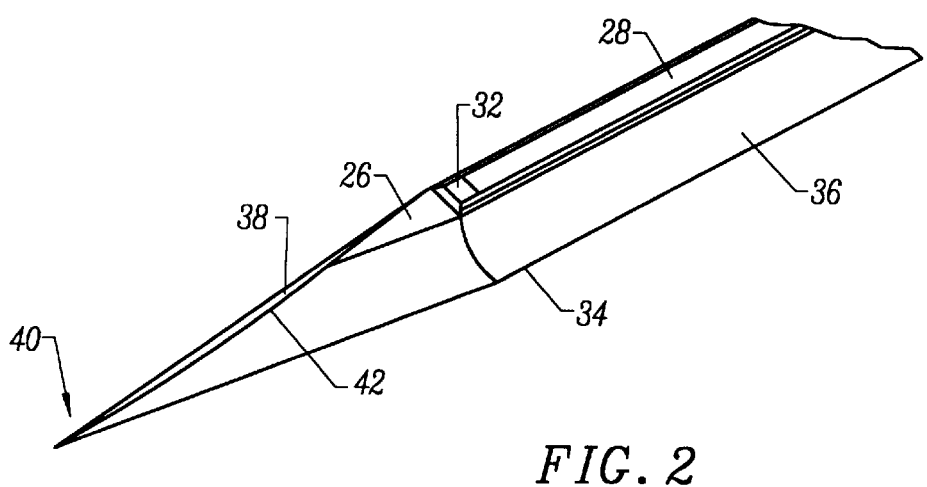
FIG. 2 is an enlarged view of the tip of the probe shown in FIG. 1.

FIG. 2 is an enlarged view of the distal end or tip 40 of the elongated body 22. The figure illustrates the top surface 26, the channel cap 28, the channel cap outlet port 32, the bottom surface 34, the first side wall 36, and the second side wall 38. Observe that the bottom surface 34 converges into the tip 40. In particular, the bottom horizontal surface 34 horizontally converges into the tip 40. Since isotropic etching techniques are used, the tip 40 can be near infinitesimally small.

FIG. 2 also illustrates that the first side wall 36 converges into the tip 40, as does the second side wall 38. In particular, each side wall 36 and 38 horizontally and vertically converges into the tip 40 in a smooth manner, without any step transitions. The first side wall 36 and the second side wall 38 meet one another to form a rib 42, which smoothly extends into the tip 40.

The tip 40 formed in accordance with the present invention is sharper than prior art probes because the processing to form the tip allows for a tip which originates from a nearly infinitesimal point that tapers to the full dimensions of the elongated body 22.

Figure 3:
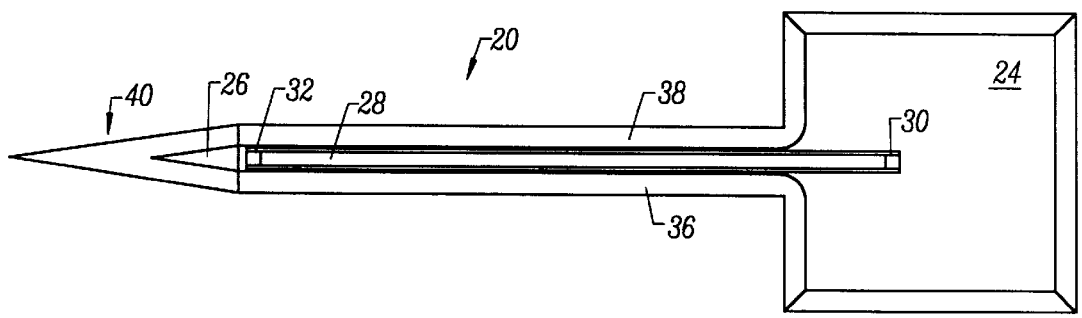
FIG. 3 is a top view of the probe shown in FIG. 1.

FIG. 3 is a top view of the isotropically etched probe 20. The figure clearly shows the previously described elements, including the shank end 24, the top surface 26, the channel cap 28, the channel cap inlet port 30, the channel cap outlet port 32, the first side wall 36, the second side wall 38, and the tip 40.

Figure 4:
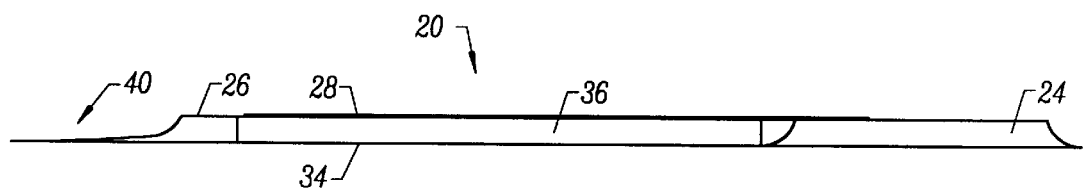
FIG. 4 is a side view of the probe shown in FIG. 1.

FIG. 4 is a side view of the probe 20. The figure shows the shank end 24, the top surface 26, the channel cap 28, the bottom surface 34, the first side wall 36, and the tip 40. Observe the curved surface leading to the tip 40. This smooth surface, without abrupt step transitions is attributable to the isotropic etching operation used in accordance with the invention.

Figure 5:
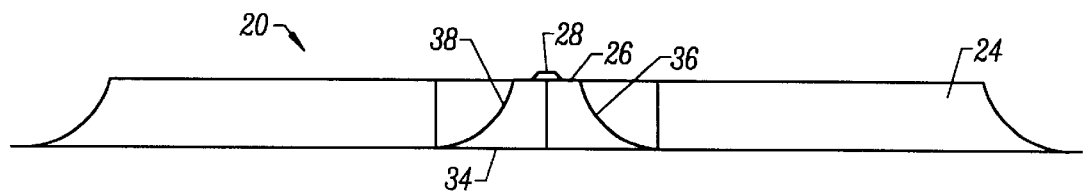
FIG. 5 is a front view of the probe shown in FIG. 1.

FIG. 5 is a front view of the probe 20. The figure shows the shank end 24, the top surface 26, the channel cap 28, the bottom surface 34. The figure also shows curved side walls 36 and 38. The curved sidewalls avoid abrupt step transitions associated with prior art probes. The curved sidewalls are attributable to the isotropic etching operation of the invention.

Figure 6:
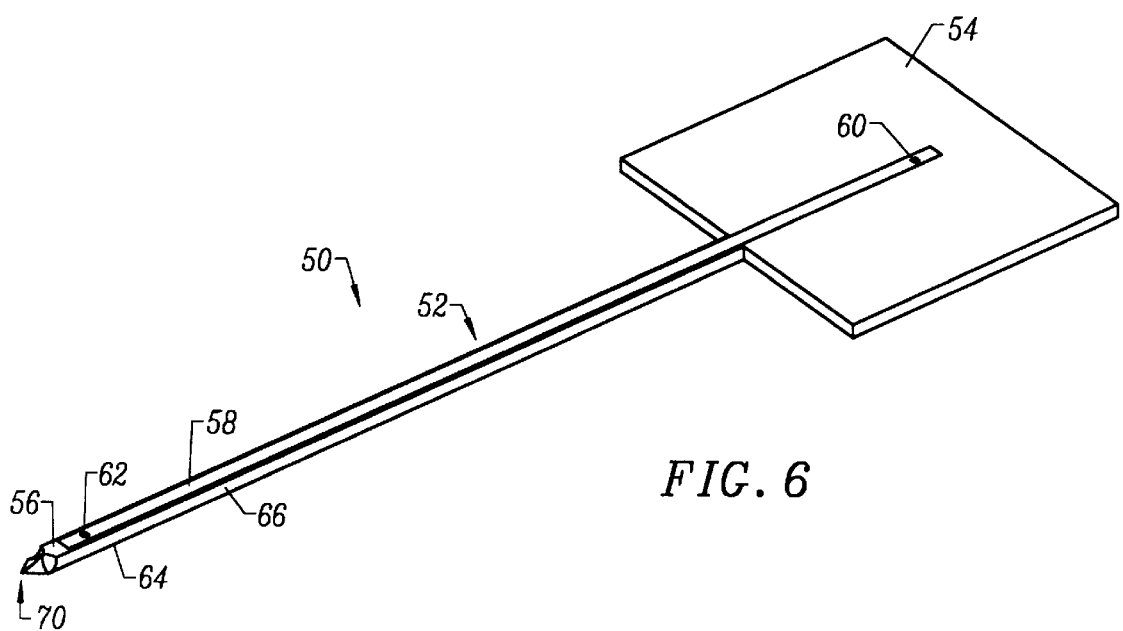
FIG. 6 is a perspective view of an isotropically and anisotropically etched probe in accordance with an embodiment of the invention.

FIG. 6 is a perspective view of an isotropically/anisotropically etched probe 50 in accordance with another embodiment of the invention. The probe 50 includes an elongated body 52 which terminates in a shank end 54. The device includes a top horizontal surface 56, which supports a channel cap 58. The channel cap 58 includes a channel cap inlet port 60 and a channel cap outlet port 62. FIG. 6 also shows a first vertical side wall 66, positioned between the top horizontal surface 56 and a bottom horizontal surface 64. A second vertical side wall (not shown) exists on the other side of the device.

Figure 7:
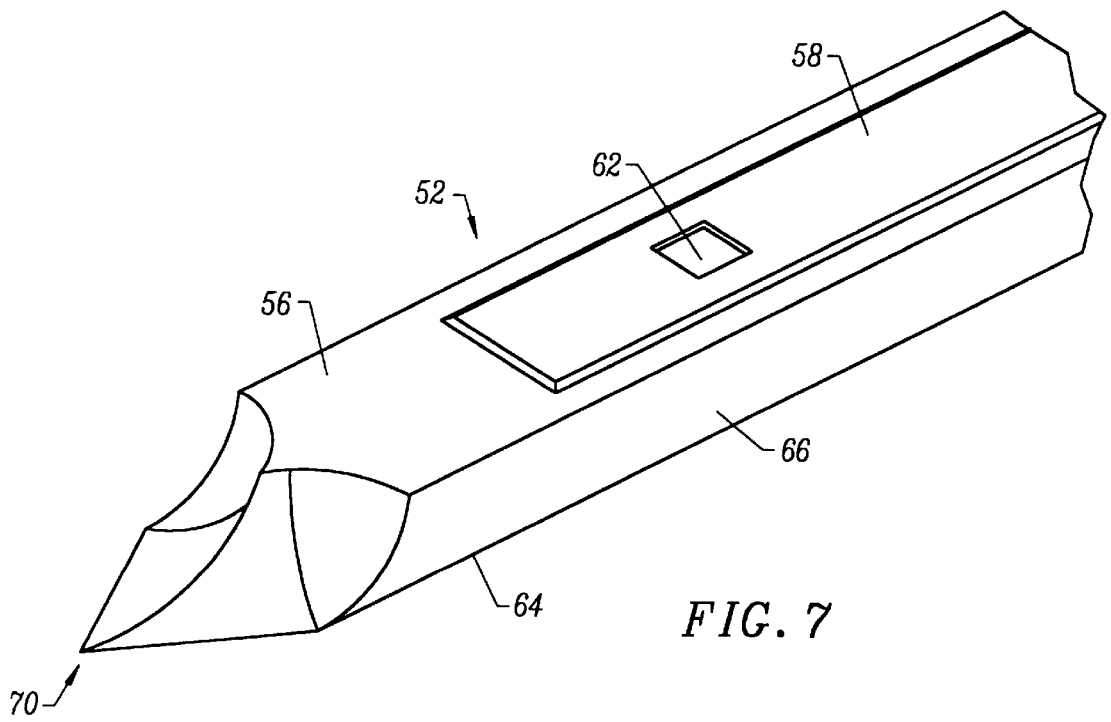
FIG. 7 is an enlarged view of the tip of the probe shown in FIG. 6.

FIG. 7 is an enlarged perspective view of the distal end or tip 70 of the elongated body 52. FIG. 7 clearly shows the vertical side wall 66, which stands in contrast to the curved sidewalls of the device of FIGS. 1–5. The tip 70 is formed using a combination of isotropic and anisotropic etching. The anisotropic etching provides the vertical side walls, while the isotropic etching provides the smooth transition into the tip 70. The tip has smooth surfaces and otherwise avoids abrupt step transitions between the tip 70 and the cross-sectional area of the elongated body 52.

Figure 8A:
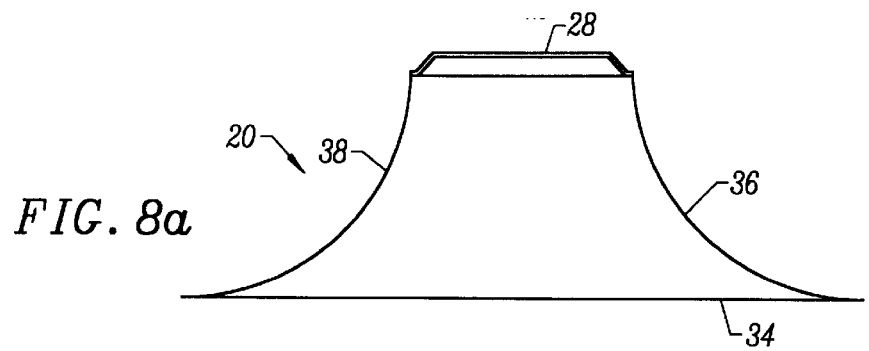
FIGS. 8a–8e illustrate different etched channels in accordance with embodiments of the invention.
Figure 8B:
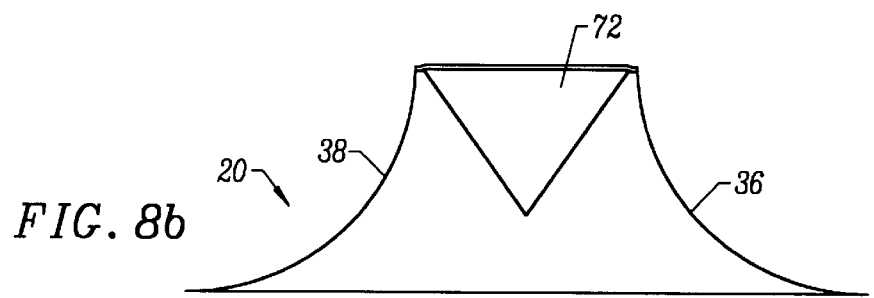
Figure 8C:
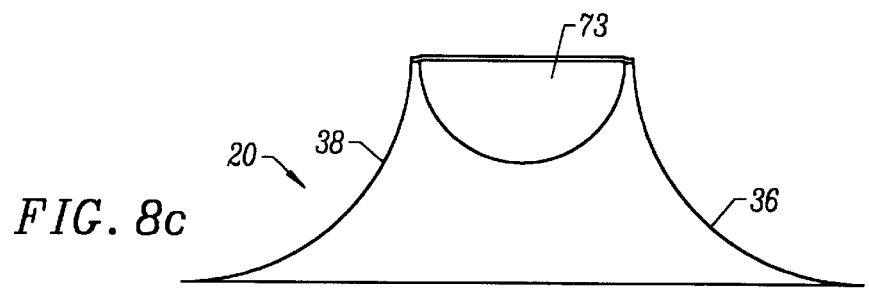
Figure 8D:
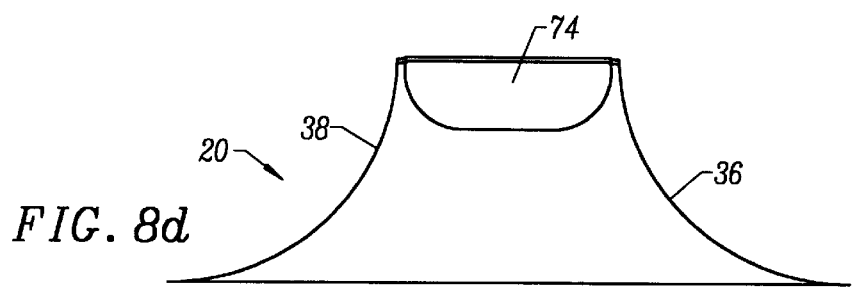
Figure 8E:
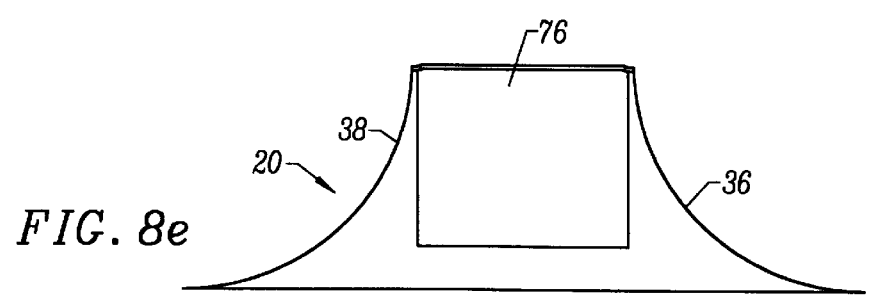

FIGS. 8a–8e illustrate different isotropically and anisotropically etched channels in accordance with different embodiments of the invention. FIG. 8a illustrates an isotropically etched probe 20 with isotropically etched sidewalls 36 and 38. The figure also shows a polysilicon shell 28. FIG. 8b is a similar figure, but shows a channel 72 formed with an anisotropic etch of a (100) silicon wafer. FIG. 8c shows a channel 73 formed with an isotropic etch. FIG. 8d shows a channel 74 isotropically etched with a flat bottom. Finally, FIG. 8e shows a channel 76 which is vertically etched.

As will be demonstrated below, the invention can be implemented using a wide variety of processing techniques. The examples provided herein are for the purpose of illustration. The invention should in no way be construed to be limited to the described examples.

Not only have a large number of processing techniques been used to implement the invention, but a variety of devices sizes have also been used. By way of example, the devices of FIGS. 8a–8e were implemented as 300μm wide and 100μm thick devices. The elongated body 52 of FIG. 6 has been implemented as a 100μm square cross-sectional device. A vertically etched trench formed through a double sided alignment and etching technique has resulted in 290μm wide and 100μm thick devices. Double sided alignment and etching on a standard thickness (500μm) wafer has produced devices that are 640μm wide and 120μm thick. In general, the invention is implemented with an elongated body that is less than approximately 700μm wide and less than approximately 200μm thick. More preferably, the invention is implemented with an elongated body that is less than approximately 300μm wide and less than approximately 150μm thick. In the case of a blade, the width of the blade can be approximately 3 mm, and its thickness can be as high as 400μm.

Advantageously, many of the processing techniques described below use silicon-on-insulator (SOI) wafers. The fabrication of probes using SOI wafers greatly simplifies processing. The type of SOI wafers typically used to fabricate the probes described in the application are comprised of two silicon wafers that are bonded together through an intermediate insulator material, typically silicon dioxide. The top wafer (device wafer) is thinned to the desired thickness of the probe using a combination of grinding and polishing techniques. The role of the bottom wafer (handle wafer) is to provide a strong substrate for easy handling.

Since the fabrication of the probe is done solely on the device layer, the purpose of the insulator material is to provide an etch stop to prevent etching into the handle layer.

Suppliers are able to provide SOI wafers with a specified overall thickness, a specified device layer thickness, and a specified thickness of insulating layer. The availability of SOI wafers permits the use of standard integrated circuit processing equipment since the overall thickness of the wafer is the same as a standard wafer. Also, the thickness of the needles can be better controlled since SOI wafer suppliers are able to guarantee a device layer thickness to within a few micrometers and this thickness is known before processing. Additionally, no wafer thinning steps, which are a common cause of probe thickness variations, beyond those of the SOI wafer supplier are required and no boron doping and EDP is required to define the probe shape. Finally, since the insulating layer provides an etch stop, the timing of the etch is not critical.

The following processing steps have been used, as described below, to construct a variety of devices, in accordance with the invention. Those skilled in the art will appreciate that a variety of modifications on the specified steps are feasible, yet still within the scope of the invention.

TABLE 1—PREFERRED FABRICATION STEPS

A. STANDARD WAFER CLEANING
Use VLSI lab sink
Piranha clean ($H_2SO_4$:$H_2O_2$, 5:1) for 10 minutes
Two, one minute rinses in de-ionized (DI) water
Rinse until resistivity of water is >11 MΩ-cm
Spin dry
Piranha clean ($H_2SO_4$:$H_2O_2$, 5:1) for 10 minutes at 120° C.
Rinse in DI water for one minute
Dip in 25:1 HF until hydrophobic
Two, one minute rinses in DI water
Rinse until resistivity of DI water is >14 MΩ-cm
Spin Dry B. CLEAN WAFERS WITH MINIMAL OXIDE STRIP
Use VLSI lab sink
Piranha clean ($H_2SO_4$:$H_2O_2$, 5:1) for 10 minutes
Rinse in DI water for one minute
Dip in 25:1 HF briefly until native silicon oxide is removed
Two, one minute rinses in DI water
Rinse until resistivity of DI water is >14 MΩ-cm
Spin Dry C. PARTIALLY CLEAN WAFERS
Use VLSI lab sink
Piranha clean ($H_2SO_4$:$H_2O_2$, 5:1) for 10 minutes
Two, one minute rinses in DI water
Rinse until resistivity of DI water is >11 MΩ-cm
Spin Dry D. DEPOSIT LOW-STRESS SILICON NITRIDE
Use a horizontal low pressure chemical vapor deposition reactor Target thickness as specified
Conditions=835° C., 140 mTorr, 100 sccm DCS, and 25 sccm $NH_3$ E. DEPOSIT PHOSPHOSILICATE GLASS (PSG)
Use a horizontal low pressure chemical vapor deposition reactor Target thickness as specified Conditions=450° C., 300 mTorr, 60 sccm SiH$_4$, 90 sccm O$_2$ and 5.2 sccm PH$_3$

G. DENSIFY LPCVD OXIDE

F. DEPOSIT LOW TEMPERATURE OXIDE (LTO)

Use a horizontal low pressure chemical vapor deposition reactor

Target thickness as specified

Conditions=450° C., 300 mTorr, 60 sccm SiH$_4$, and 90 sccm O$_2$

G. DENSIFY LPCVD OXIDE

Use horizontal atmospheric pressure reactor

Conditions=950° C., N$_2$, 1 hour; alternately, 1100° C. with a stream environment rather than N$_2$ H. PHOTOLITHOGRAPHY
1. HMDS prime
2. Photoresist coat: Coat 1 µm of Shipley S3813 (thickness may need to be varied depending on topography and thickness of material to be etched) multi-wavelength positive resist
3. Expose resist: G-line wafer stepper, standard exposure time
4. Resist develop: Standard develop using Shipley MF319
5. Hard bake for 30 minutes I. COAT BACKSIDE WITH PHOTORESIST
1. HMDS prime
2. Photoresist coat: Coat 1 µm of Shipley S3813 (thickness may need to be varied depending on topography and thiclkness of material to be etched) multi-wavelength positive resist
3. Resist develop: Standard develop using Shipley MF 319
4. Hard bake for 30 minutes

J. OXIDE WET ETCHING

Use VLSI lab sink

Etch in 5:1 BHF until desired amount of oxide has been removed

Two, one minute rinses in DI water

Rinse until resistivity of water is >11 MΩ-cm

Spin dry

K. RESIST STRIP

Use lab sink

PRS-2000, heated to 90° C., 10 minutes

Rinse in three baths of DI water, 2 minutes each

C. PARTIAL CLEAN WAFERS

L. NITRIDE ETCH

SF$_6$+He plasma etch

Etch until desired amount of nitride has been removed

M. DEPOSIT UNDOPED POLYSILICON

Use horizontal low pressure chemical vapor deposition reactor

Target thickness as specified

Conditions=605° C., 555 mTorr, and 125 sccm SiH$_4$; alternately,
580° C., 300 mTorr, and 100 sccm SiH$_4$

N. POLYSILICON ETCH

Chlorine plasma etch

Etch until desired amount of polysilicon has been removed

O. ISOTROPIC SILICON ETCH

Use lab sink

Submerge in silicon etchant (64% HNO$_3$/33%H$_2$O/3% NH$_4$F) until desired amount of silicon has been removed Rinse in DI water for 1 hour (Various concentrations of NH$_4$F will work. In addition, there are many isotropic etches involving HF, HNO$_3$, and C$_2$H$_4$O$_2$ and etches involving HF, HNO$_3$, XeF$_2$, SF$_6$ and H$_2$O that may be used in connection with the invention.)

P. ANISOTROPIC WET ETCH

Use lab sink, heated bath 750 g KOH: 1500 ml H$_2$O; many concentrations of KOH may be used to give faster/slower etch rates and higher/lower selectivity of silicon over oxide Temperature 80° C.

Q. OXIDE REMOVAL WET ETCHING

Use lab sink

Etch in diluted HF or buffered HF until desired oxide is removed

Rinse in deionized water for approximately one hour

R. NEAR VERTICAL WALLED TRENCH ETCH

Use inductively coupled plasma etcher

Advanced silicon etch process

High plasma density low pressure processing system

Fluorine plasma

Etch to desired depth

S. OXIDE, PSG, AND SILICON NITRIDE ETCH

Use lab sink

Concentrated HF dip with surfactant if needed, continue until desired sacrificial material has been removed Rinse for 2 minutes in two tanks of DI water Rinse for 120 minutes in third tank of DI water

T. SPUTTER GOLD

Use low pressure chamber

Gold target

U. GOLD ETCH

Use lab sink

Aqua regent etchant or other commercially available gold etchant

V. WET OXIDATION

Use horizontal atmospheric pressure reactor

Conditions=Temperature as specified, water vapor environment

W. BORON DIFFUSION

Use horizontal atmospheric pressure reactor

Solid source boron diffusion

Conditions=Temperature as specified

X. DEPOSIT IN SITU DOPED POLYSILICON

Use horizontal low pressure chemical vapor deposition reactor

Target thickness as specified

Conditions=610° C. and 300 mTorr

Y. GROW THERMAL OXIDE

Use horizontal atmospheric pressure reactor

Conditions=1050° C., steam environment

Z. FUSION BOND WAFERS

Horizontal atmospheric pressure reactor

Conditions=1100° C., nitrogen environment

EXAMPLE I

Figure 9A:
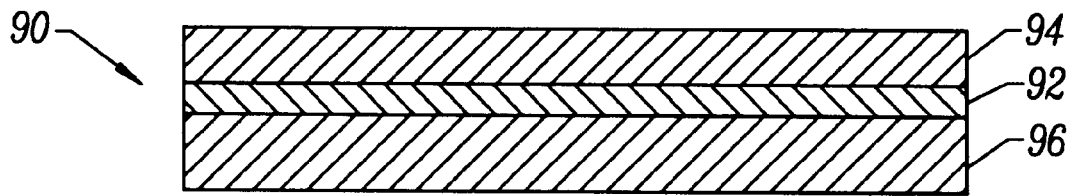
FIGS. 9a–9e illustrate the construction of a probe in accordance with a first example of the invention.
Figure 9B:
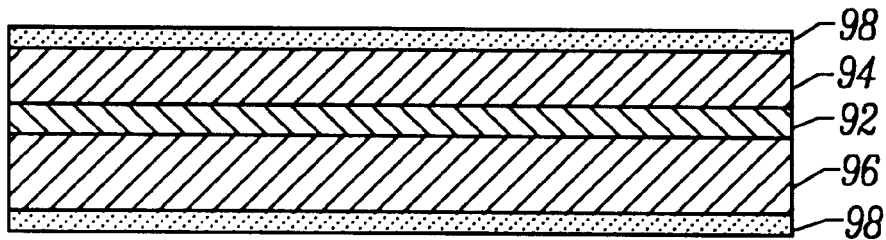

FIGS. 9a–9e illustrate the process flow for constructing an isotropically etched probe fabricated on a Silicon On Insulator (SOI) wafer. FIG. 9a illustrates an SOI wafer 90 including an insulator layer 92 sandwiched between a device wafer 94 and a handle wafer 96. The device wafer 94 is formed of single crystal silicon with a thickness of approximately 100 μm. The orientation is (100) or (110). The insulator 92 is thermally grown $SiO_2$, which is 1 to 2 μm thick, but may also be silicon nitride and/or chemically deposited oxide. The handle wafer 96 is approximately 500 μm thick single crystal silicon with a (100) orientation. Since the handle wafer 96 is formed of single crystal silicon it has the same hatching as the device wafer 94, which is also formed of single crystal silicon.

Figure 9C:
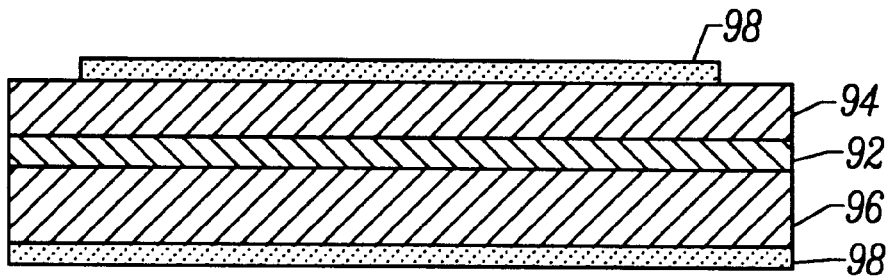
Figure 9D:
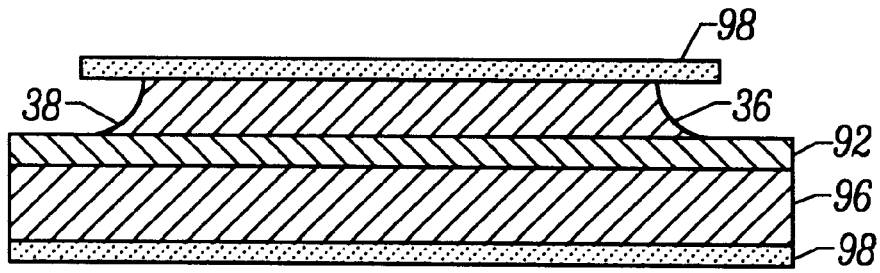

After the wafer 90 is cleaned (step A), an approximately 0.5 μm thick layer of silicon nitride (step D) is deposited. The silicon nitride 98, shown in FIG. 9b, serves as the masking material for the silicon isotropic etch. The silicon nitride 98 is then patterned (step H), etched (step L), and the photoresist is stripped (step K). The resulting structure is shown in FIG. 9c. The device is subsequently submerged in the isotropic silicon etchant (step O), producing the device shown in FIG. 9d. Observe that this operation produces smooth side walls 36 and 38 of the type shown in FIGS. 1–5. It should be appreciated that FIGS. 9a–9e are a front cross-sectional view of the probe 20 in approximately the center of the elongated body 22. The same processing generates the previously disclosed tip 40.

Figure 9E:
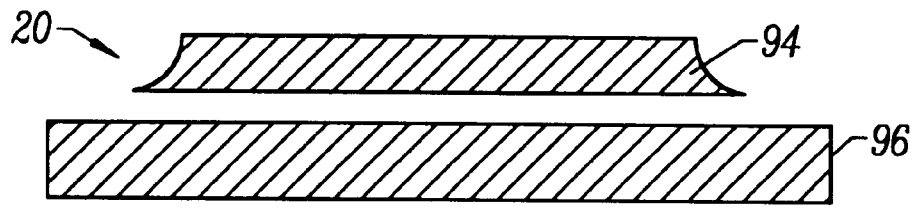

The silicon nitride is then removed and the probe is released (step S). FIG. 9e illustrates the released probe 20. The device is then rinsed in deionized water for approximately one hour. The resultant device, which does not include a channel, is a probe for use as a lancet.

EXAMPLE II

Figure 10A:
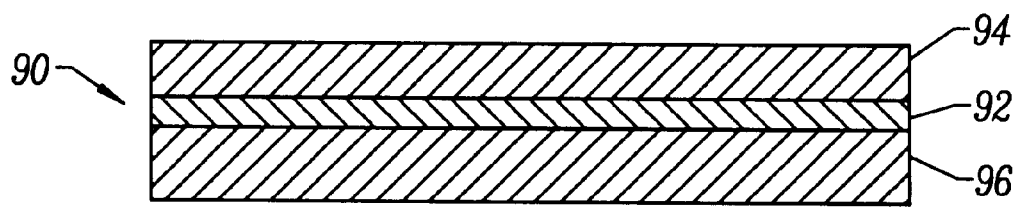
FIGS. 10a–10i illustrate the construction of a probe in accordance with a second example of the invention.
Figure 10B:
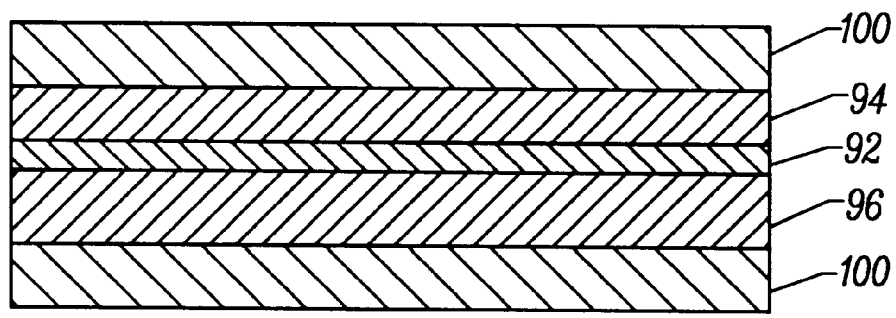
Figure 10C:
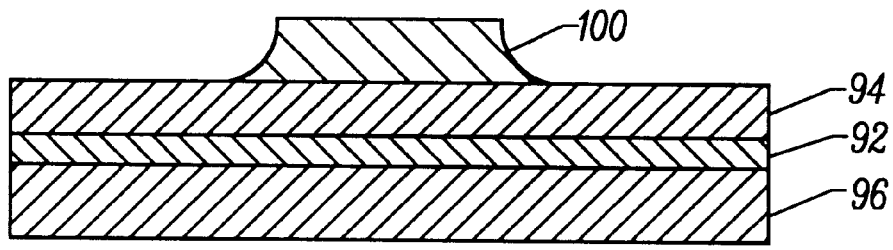
Figure 10D:
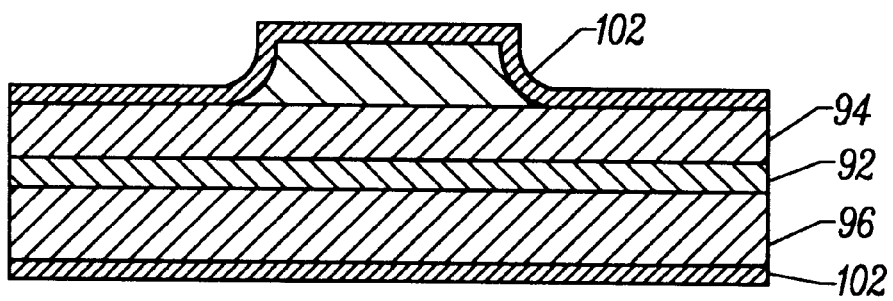
Figure 10E:
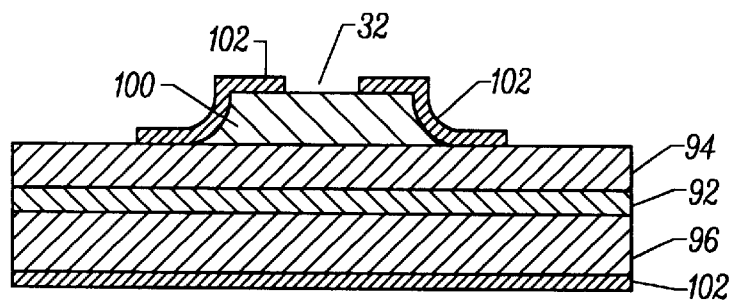
Figure 10F:
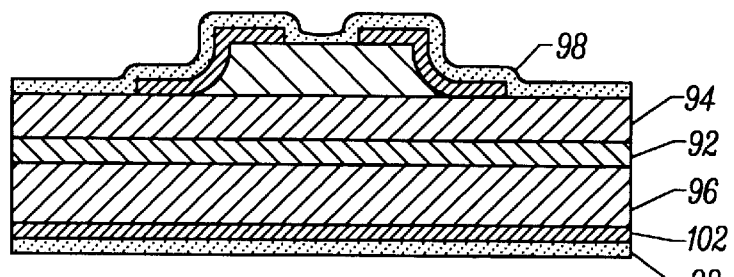
Figure 10G:
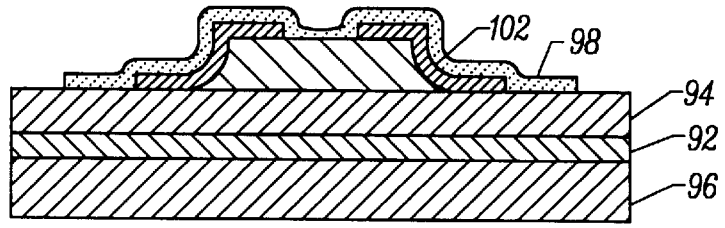

FIGS. 10a–10i illustrate the process flow to construct an isotropically etched probe with a surface micromachined fluid channel fabricated on an SOI wafer. FIG. 10a illustrates a device of the type shown and described in reference to FIG. 9a. The wafer is cleaned (step A). Then, an approximately 2 μm thick layer of phosphosilicate glass is deposited (step E). FIG. 10b shows the phosphosilicate glass 100, which is used as the sacrificial channel material. The phosphosilicate glass 100 is then patterned (step H), etched (step J), and the photoresist is stripped (step K) to form the mold to make the fluid channel. The resultant device is shown in FIG. 10c. The device is then cleaned (step B) and an approximately 2 μm layer of polysilicon is deposited (step M) to form the frame material of the channel cap. The polysilicon 102 is shown in FIG. 10d. The polysilicon 102 is then patterned (step H), etched (step N), and the resist is stripped (step K). This results in the previously described channel cap inlet port and the channel cap outlet port. In addition, this operation removes the polysilicon away from the edge of the shell. The resultant structure is shown in FIG. 10e. The region 32 between the two polysilicon 102 members is the channel cap outlet port.

The wafer is then cleaned (step B). A 0.5 μm thick layer of silicon nitride is then deposited (step D). The silicon nitride 98, shown in FIG. 10f, operates as the masking material for the silicon isotropic etch. The silicon nitride 98 is then patterned (step H), etched (step L), and the resist is stripped (step K), resulting in the device shown in FIG. 10g.

Figure 10H:
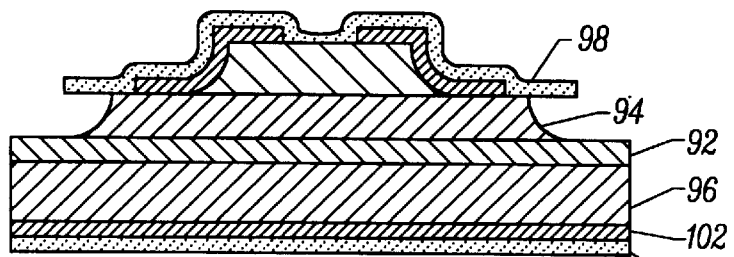

The device is then submerged in an isotropic silicon etchant (step O), producing the device shown in FIG. 10h. Once again observe the first and second curved side walls 36 and 38 formed by this operation. This operation also produces the previously described tip structure.

Figure 10I:
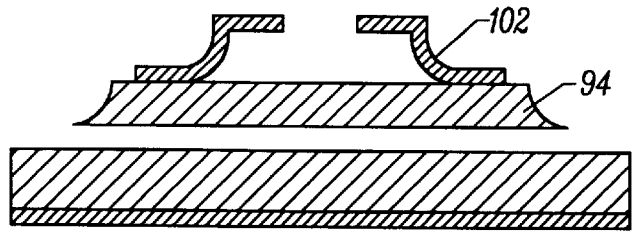

The silicon nitride is then removed (step S), the probe is released, and the phosphosilicate glass is removed to produce the device shown in FIG. 10i. The device is then rinsed in deionized water for approximately one hour.

EXAMPLE III

Figure 11A:
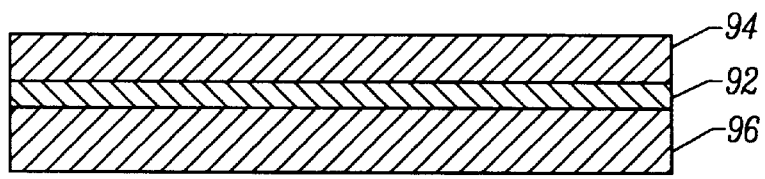
FIGS. 11a–11L illustrate the construction of a probe in accordance with a third example of the invention.
Figure 11B:
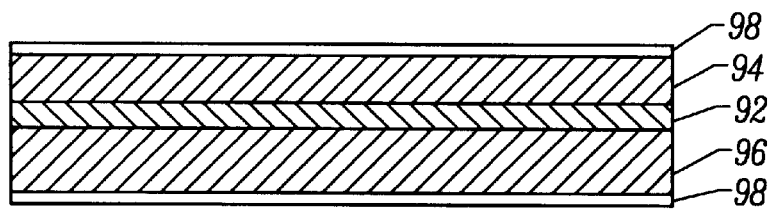
Figure 11C:
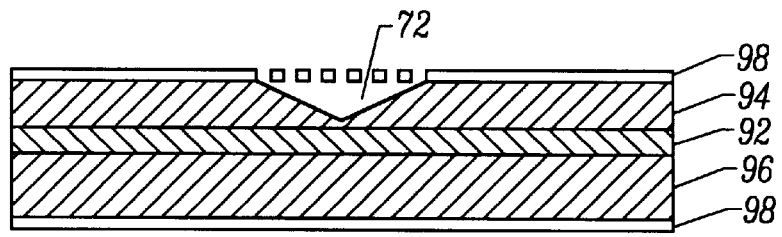

FIGS. 11a–11L illustrate process flow for an isotropically shaped probe incorporating an anisotropic etch to form a channel, as fabricated on an SOI wafer. The starting device of FIG. 11a is of the type described in the previous examples. The wafer is cleaned (step A) and approximately 0.5 μm of silicon nitride is deposited (step D), resulting in the device shown in FIG. 11b. Alternately, a 0.5 μm thick layer of thermal oxide can replace the 0.5 μm thick layer of silicon nitride. The oxide layer is etched using $CF_4+CHF_3+$ He plasma etch and 4:1 $H_2O$:KOH solution at 40° C. The silicon nitride is then patterned (step H), etched (step TL), and the resist is stripped (step K). The single crystal silicon (100) is then subjected to an anisotropic etchant (step P) to form an anisotropically etched trench 72 for a fluid passage, as shown in FIG. 11c.

Figure 11D:
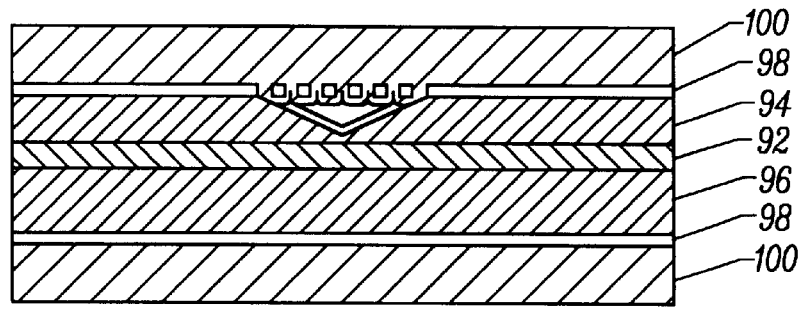
Figure 11E:
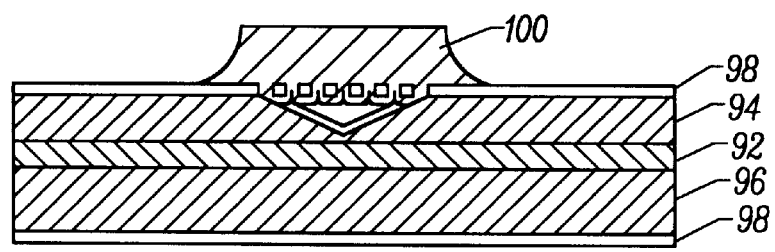

The wafer is then cleaned (step A) and approximately 2 μm of phosphosilicate glass is deposited (step E) to fill openings in the silicon nitride masking layer 98, as shown in FIG. 11d. It may be preferable to perform a 3 μm thick deposition of PSG and a higher temperature densification of the PSG than is specified by Step G. A more suitable densification is 2 hours, 1100° C. in an ambient stream. Since it is desirable to minimize the high temperature steps in cases where circuitry is involved, a densification at temperatures closer to 950° C. should be done. The phosphosilicate glass 100 is then patterned (step H), etched (step J), and the resist is stripped (step K) to expose regions of the silicon nitride 98, as shown in FIG. 11e.

Figure 11F:
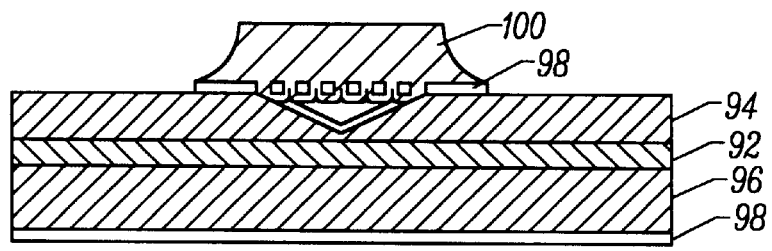
Figure 11G:
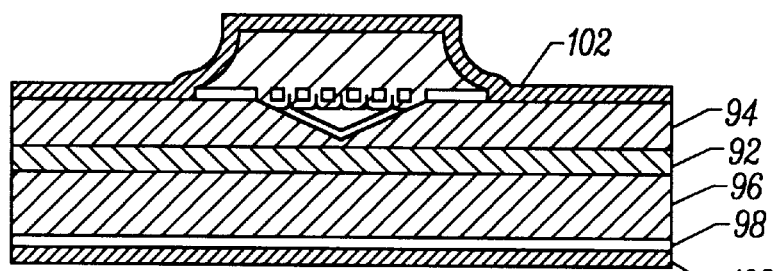
Figure 11H:
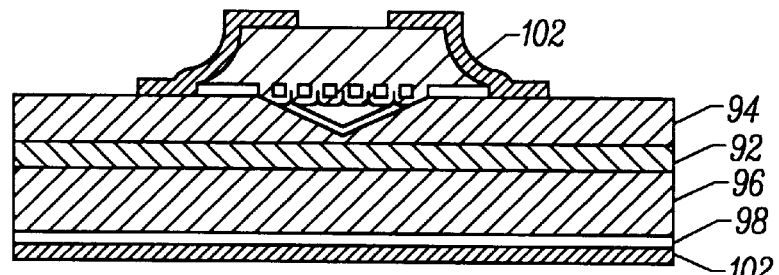

The silicon nitride 98 is then etched (step L), resulting in the device shown in FIG. 11f. The resist can typically be removed before the nitride etch since the phosphosilicate glass acts as an etch mask. In some cases, the thickness of the phosphosilicate glass may not be thick enough to prevent the etch from attacking the underlying nitride, in which case, photoresist may be necessary.

Figure 11I:
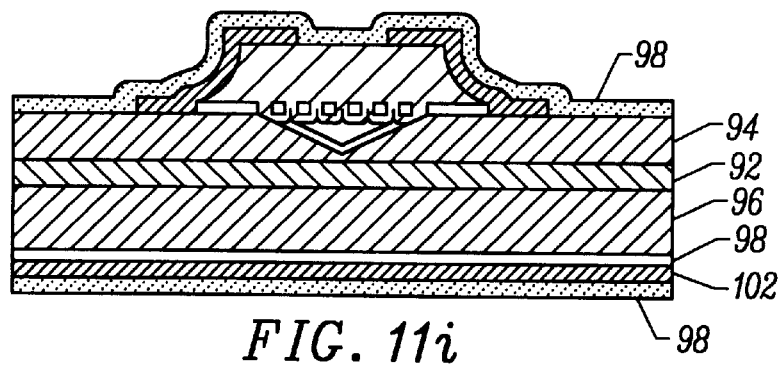

The wafer is then cleaned (step B). Approximately 2 μm of polysilicon is then deposited (step M) to form the frame material of the channel cap, resulting in the device shown in FIG. 11g. The device is then patterned (step H), etched (step N), and the photoresist is stripped (step K) to form the channel cap inlet and outlet ports and to remove the polysilicon away from the edge of the shell. This processing results in the device shown in FIG. 11h. The wafer is then cleaned (step B) and approximately 0.5 μm of silicon nitride is deposited (step D). The silicon nitride 98, as shown in FIG. 11i, is used as the masking material for the silicon isotropic etch.

Figure 11J:
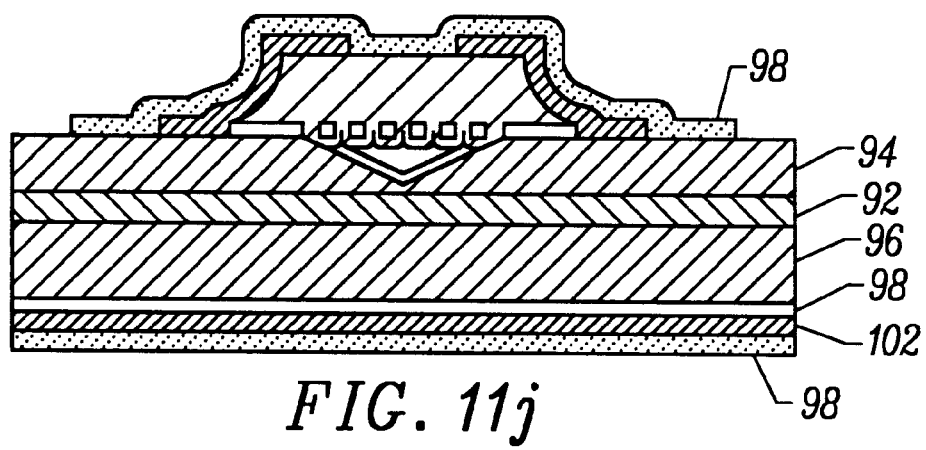
Figure 11K:
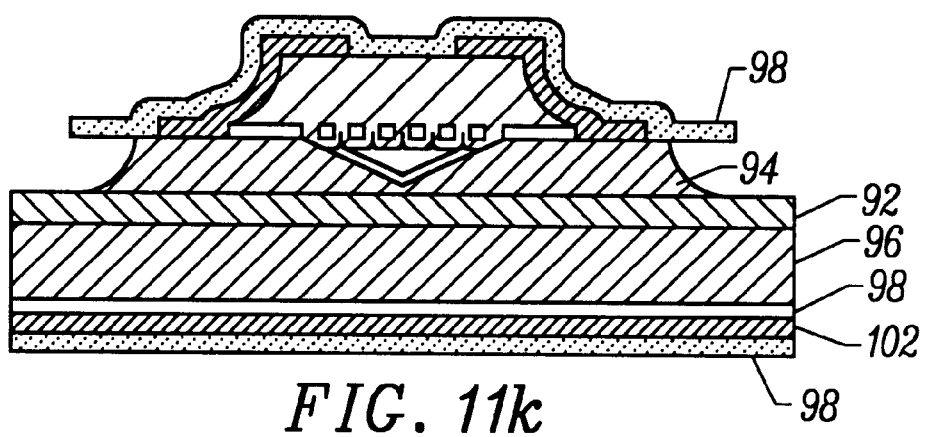
Figure 11L:
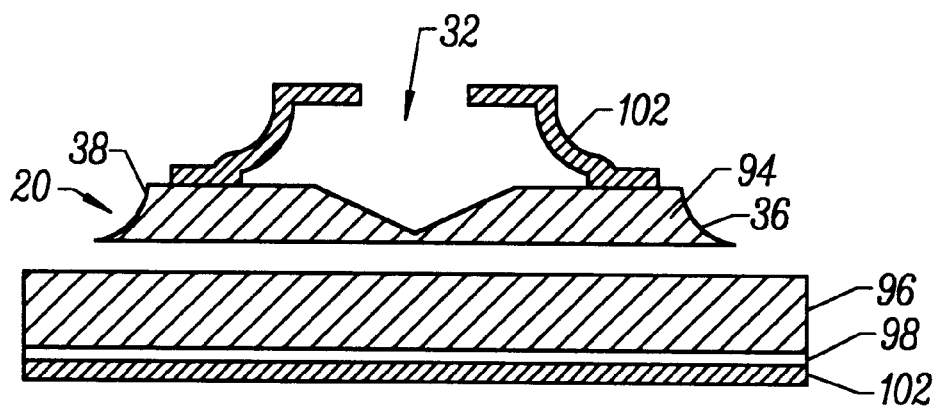

The silicon nitride is then patterned (step H), etched (step L), and the resist is stripped (step K), resulting in the structure shown in FIG. 11j. The device is then submerged in an isotropic silicon etchant (step O), producing the structure of FIG. 11k. The silicon nitride is then removed, the probe is released, and the phosphosilicate glass is removed (step S). The resulting device, shown in FIG. 11L is then rinsed in deionized water for approximately one hour.

EXAMPLE IV

Figure 12A:
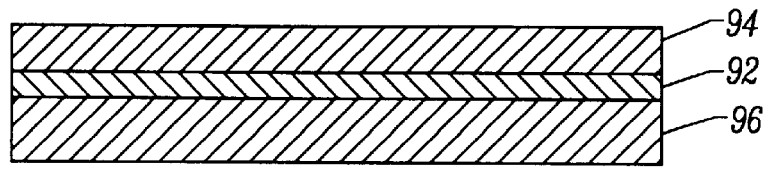
FIGS. 12a–12L illustrate the construction of a probe in accordance with a fourth example of the invention.
Figure 12B:
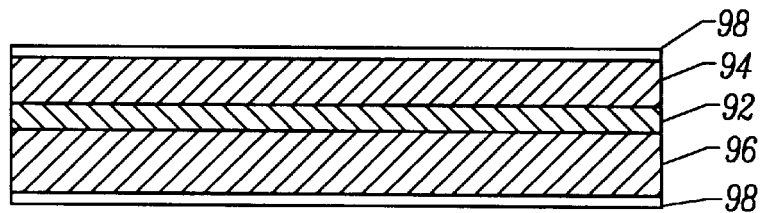
Figure 12C:
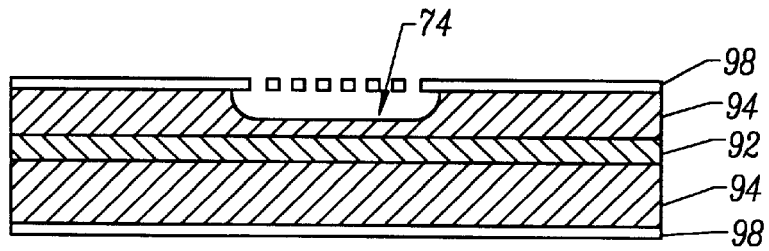

FIGS. 12a–12L illustrate process flow for an isotropically shaped probe incorporating an isotropic etch to form a channel, as fabricated on an SOI wafer. The starting device of FIG. 12a is of the type described in the previous examples. The wafer is cleaned (step A) and approximately 0.5 μm of silicon nitride is deposited (step D), resulting in the device shown in FIG. 12b. The silicon nitride is then patterned (step H), etched (step L), and the resist is stripped (step K). The single crystal silicon (100) is then subjected to an isotropic etchant (step O) to form an isotropically etched flat-bottom trench 74 for a fluid passage, as shown in FIG. 12c.

Figure 12D:
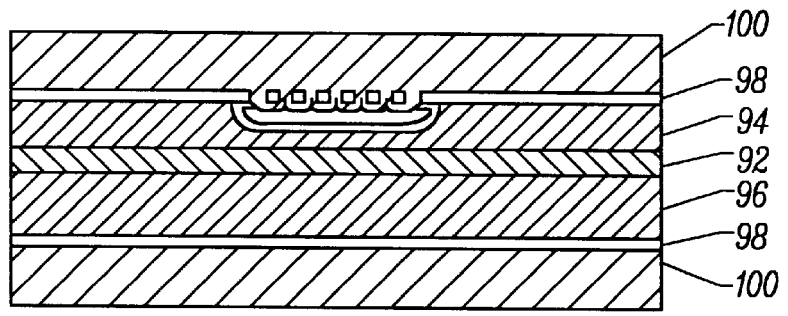
Figure 12E:
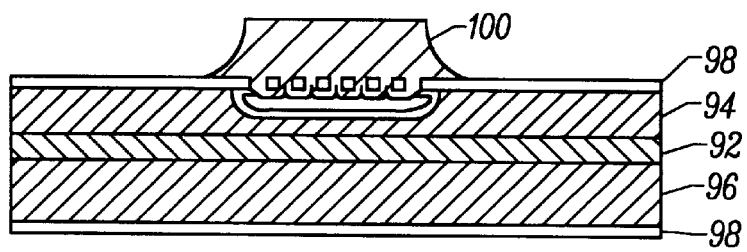

The wafer is then cleaned (step A) and approximately 2 μm of phosphosilicate glass is deposited (step E) to fill openings in the silicon nitride masking layer 98, as shown in FIG. 12d. The phosphosilicate glass 100 is then patterned (step H), etched (step J), and the resist is stripped (step K) to expose regions of the silicon nitride 98, as shown in FIG. 12e.

Figure 12F:
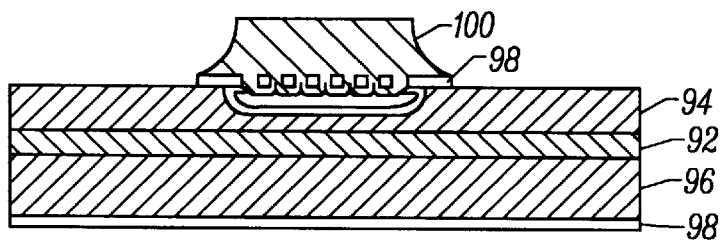
Figure 12G:
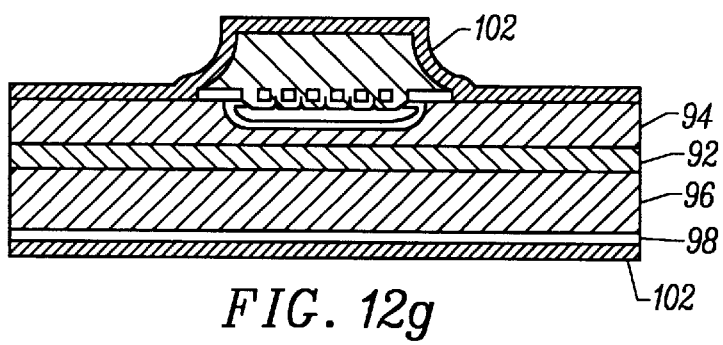
Figure 12H:
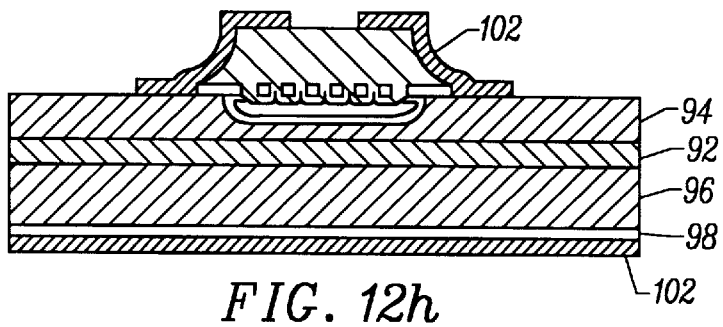

The silicon nitride 98 is then etched (step L), resulting in the device shown in FIG. 12f. The resist can typically be removed before the nitride etch since the phosphosilicate glass acts as an etch mask. In some cases, the thickness of the phosphosilicate glass may not be thick enough to prevent the etch from attacking the underlying nitride, in which case, photoresist may be necessary.

Figure 12I:
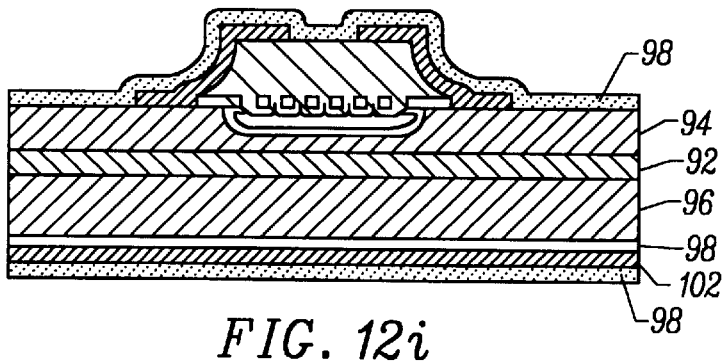

The wafer is then cleaned (step B). Approximately 2 μm of polysilicon are then deposited (step M) to form the frame material of the fluid channel, resulting in the device shown in FIG. 12g. The device is then patterned (step H), etched (step N), and the photoresist is stripped (step K) to form the fluid inlet and outlet port and to remove the polysilicon away from the edge of the shell. This processing results in the device shown in FIG. 12h. The wafer is then cleaned (step B) and approximately 0.5 μm of silicon nitride is deposited (step D). The silicon nitride 98, as shown in FIG. 12i, is used as the masking material for the silicon isotropic etch.

Figure 12J:
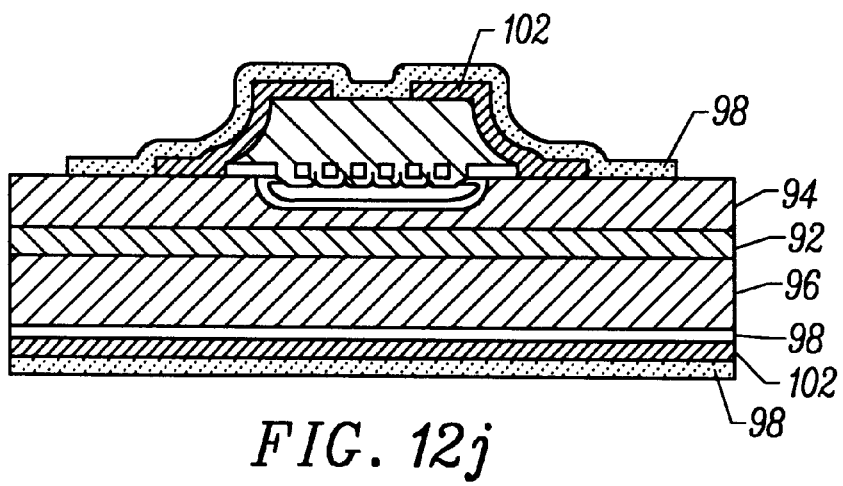
Figure 12K:
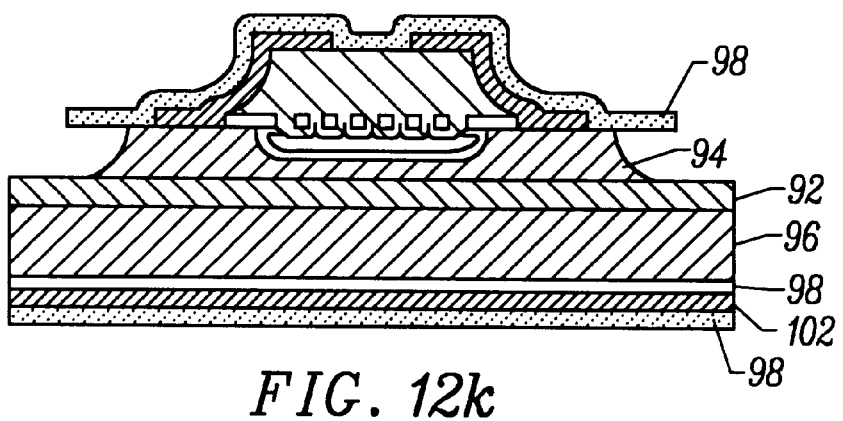
Figure 12L:
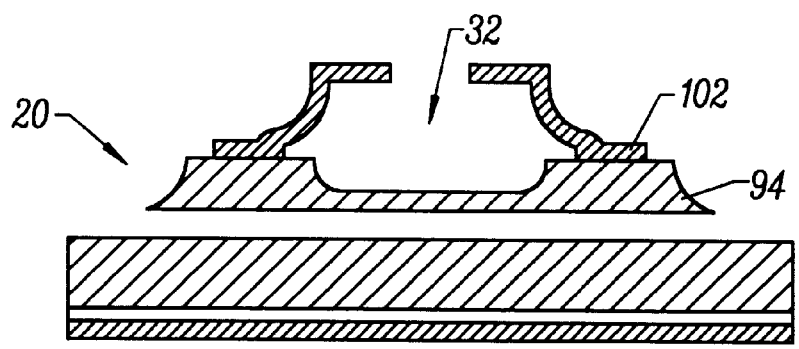

The silicon nitride is then patterned (step H), etched (step L), and the resist is stripped (step K), resulting in the structure shown in FIG. 12j. The device is then submerged in an isotropic silicon etchant (step O), producing the structure of FIG. 12k. The silicon nitride is then removed, the probe is released, and the phosphosilicate glass is removed (step S). The resulting device, shown in FIG. 12L is then rinsed in deionized water for approximately one hour.

EXAMPLE V

Figure 13A:
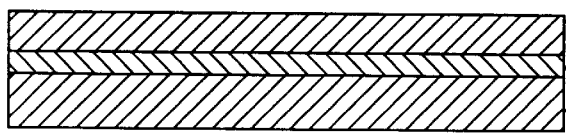
FIGS. 13a–13q' illustrate the construction of a probe in accordance with a fifth example of the invention.
Figure 13A:
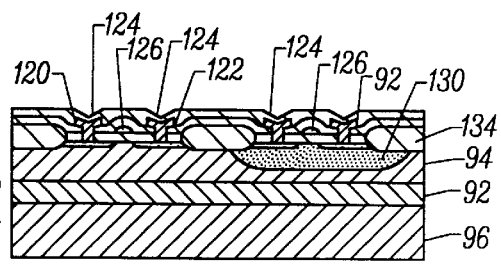
Figure 13B:
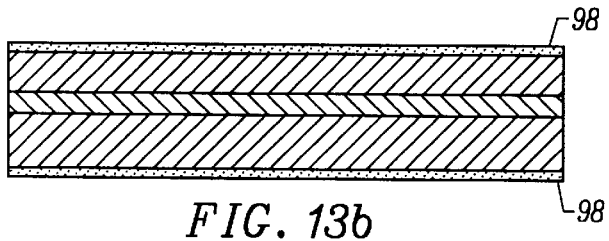
Figure 13B:
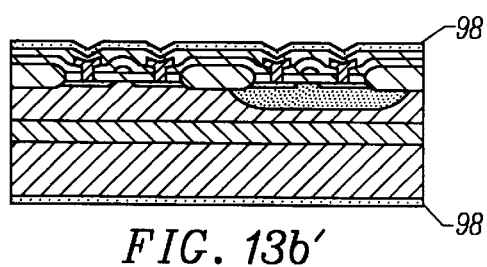
Figure 13C:
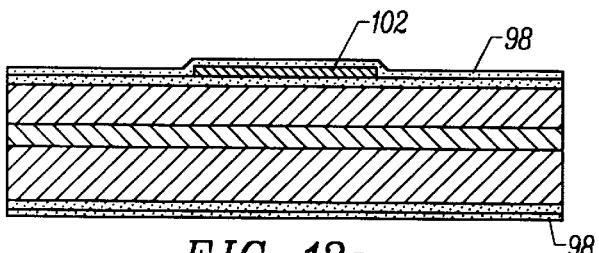
Figure 13C:
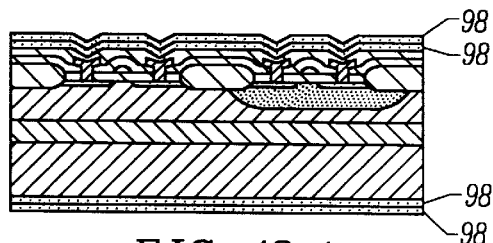
Figure 13D:
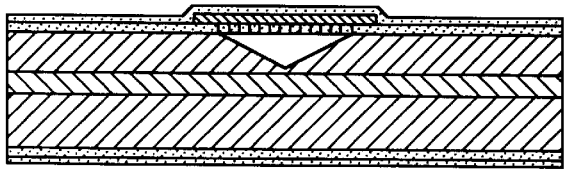
Figure 13D:
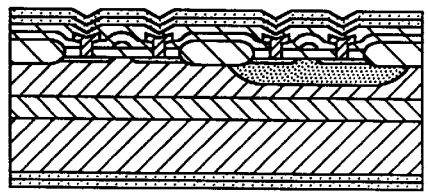
Figure 13E:
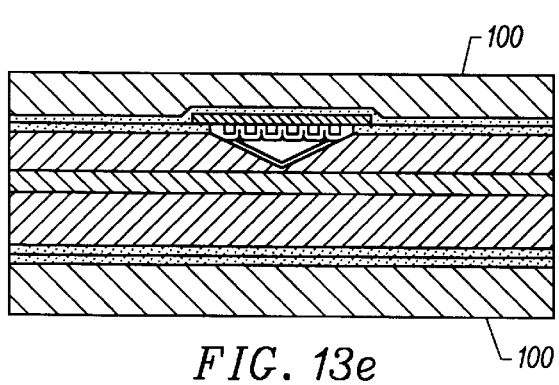
Figure 13E:
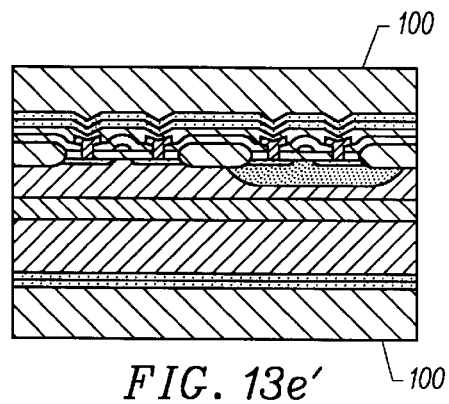
Figure 13F:
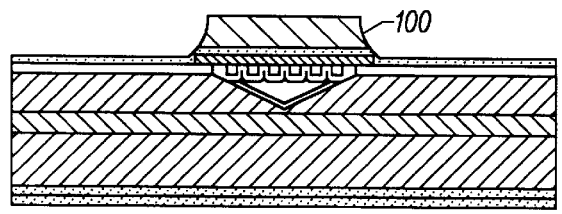
Figure 13F:
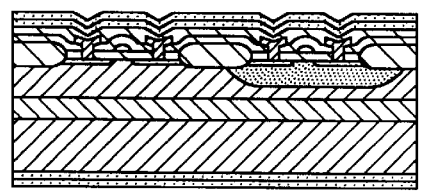
Figure 13G:
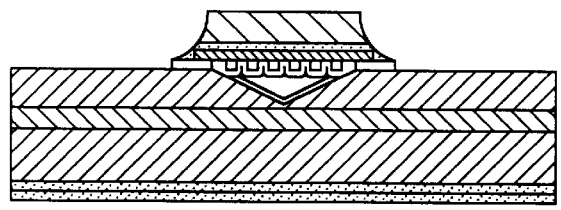
Figure 13G:
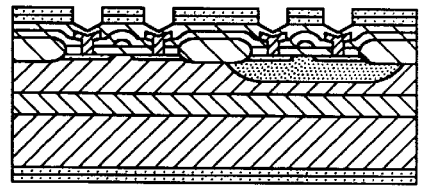
Figure 13H:
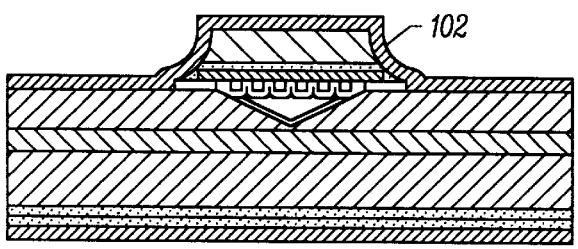
Figure 13H:
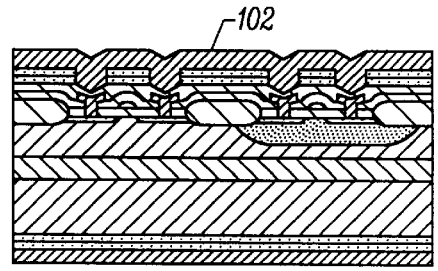
Figure 13I:
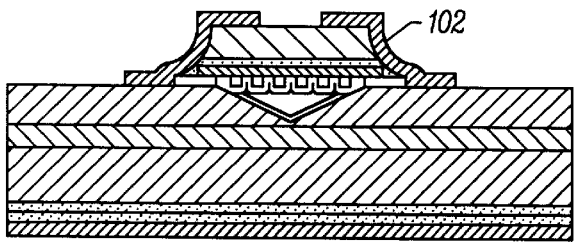
Figure 13I:
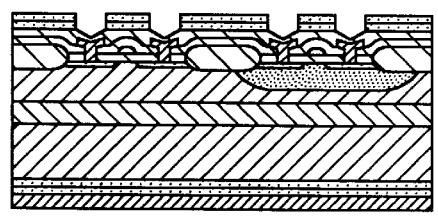
Figure 13J:
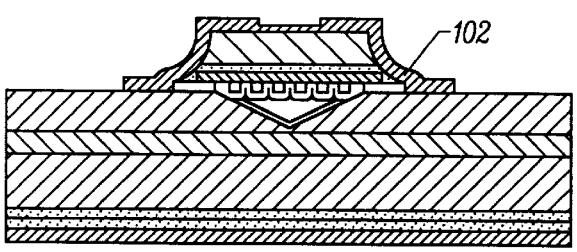
Figure 13J:
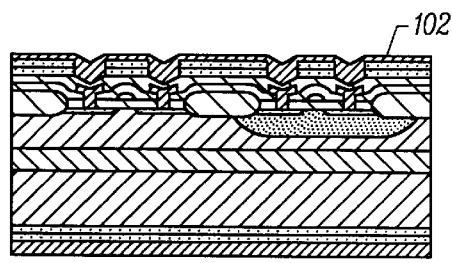
Figure 13K:
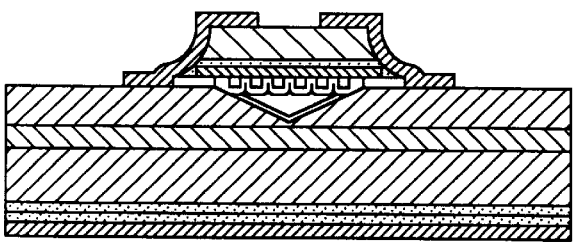
Figure 13K:
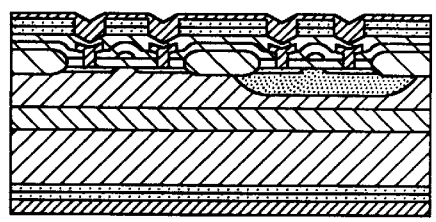
Figure 13L:
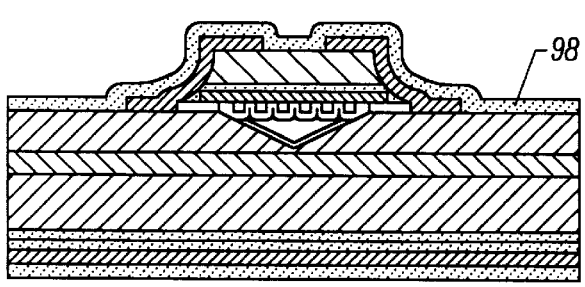
Figure 13L:
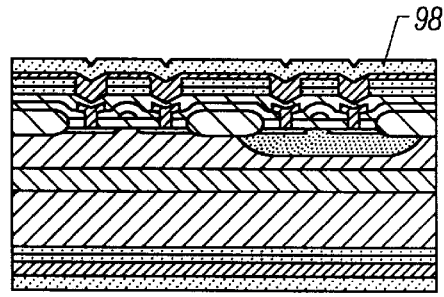
Figure 13M:
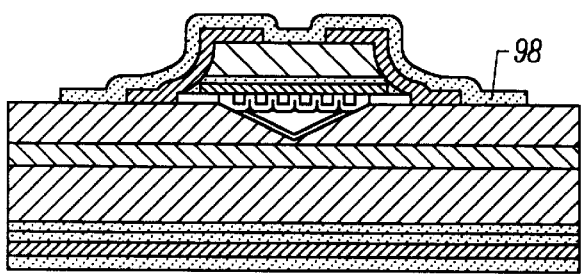
Figure 13M:
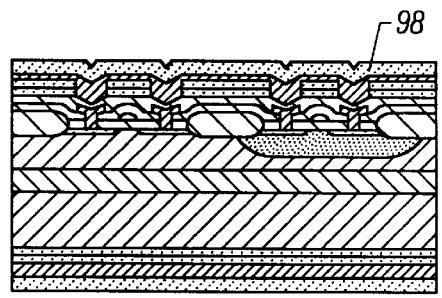
Figure 13N:
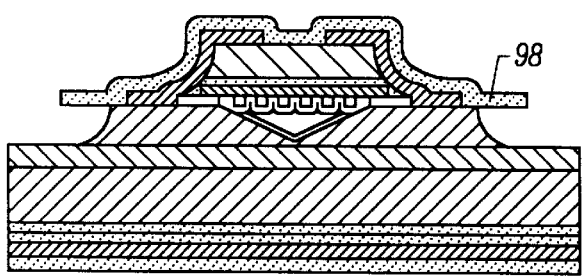
Figure 13N:
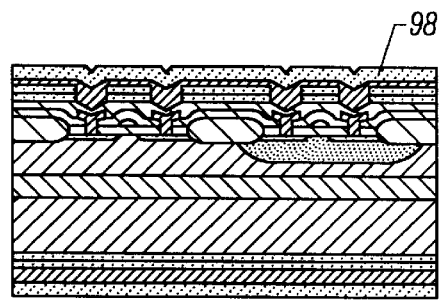
Figure 13O:
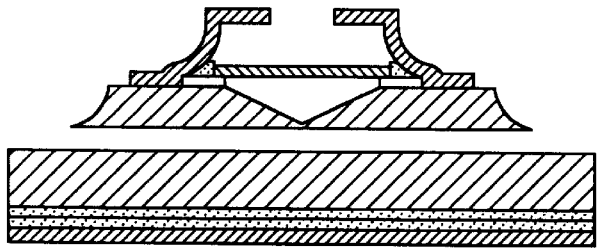
Figure 13O:
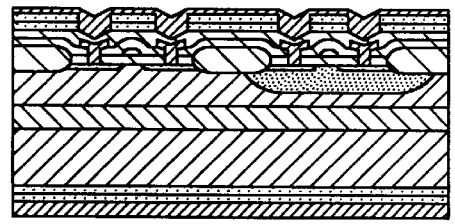
Figure 13P:
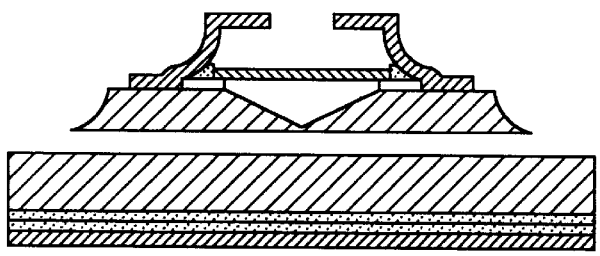
Figure 13P:
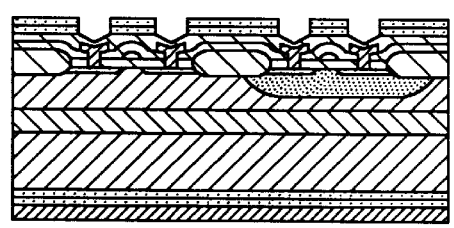
Figure 13Q:
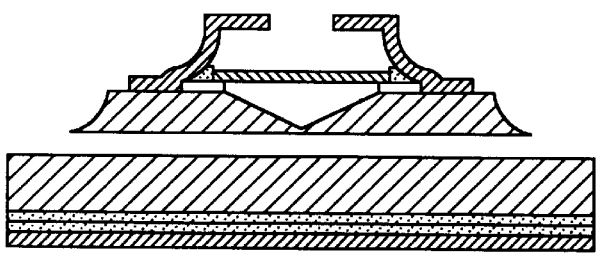
Figure 13Q:
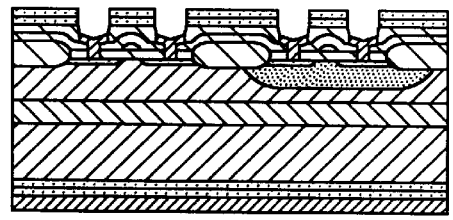

FIGS. 13a–13q' illustrate the process flow for an isotropically shaped probe incorporating an anisotropic etch to form a channel fabricated on an SOI wafer with integrated circuitry and a micromachined structure in the form of a polysilicon heater. In the following figures, the figures on the left-hand side of each page are cross-sections of the shaft, while the figures on the right-hand side of each page are cross-sections of the circuitry. FIG. 13a is a SOI wafer with (100) orientation. The left side of FIG. 13a' illustrates two p+ doped regions 120 and 122. A polysilicon contact 124 is positioned above each region. An n+ polysilicon region 126 is positioned between the contacts 124. The right side of FIG. 13a' has a similar configuration, but further includes an n well 130 and n+ regions 132. The processing used to construct a device of this type is known in the art.

The wafer is cleaned (step B) and approximately 0.5 μm of silicon nitride is deposited (step D.), resulting in the structure shown in FIGS. 13b and 13b'. The wafer is then cleaned (step B) and approximately 0.4 μm of polysilicon is deposited (step X) to form a polysilicon heater. The polysilicon is patterned (step H), etched (step N), and the resist is stripped (step K). The wafer is then cleaned (step B). Approximately 0.5 μm of silicon nitride is then deposited (step D) to protect the polysilicon during the silicon etch. The resultant structure is shown in FIGS. 13c and 13c'.

The silicon nitride is then patterned (step H), etched (step L), and the resist is stripped (step K). (A more IC compatible etch of tetramethyl ammonium hydroxide may be used in lieu of KOH). The single crystal silicon is then etched in an anisotropic etch (step P) to form a trench for a fluid passage, as shown in FIG. 13d. The wafer is then cleaned (step A) and approximately 2 μm of phosphosilicate glass is deposited (step E) to fill openings in the silicon nitride mask layer. The resultant structure is shown in FIGS. 13e and 13e'.

The device is then patterned (step H), etched (step J), and the resist is stripped (step K). This exposes regions of the silicon nitride, as shown in FIGS. 13f and 13f'. The silicon nitride is then patterned (step H), etched (step L), and the resist is stripped (step K). This operation removes the nitride from the region outside of the channel and over the electrical contact holes, as shown in FIGS. 13g and 13g'.

The wafer is then cleaned (step B) and approximately 2 μm of polysilicon (step M) is deposited to form the frame material of the fluid channel, as shown in FIGS. 13h and 13h'. The polysilicon is then patterned (step H), etched (step N), and resist is stripped (step K). This operation produces channel cap inlet and outlet ports and removes the polysilicon away from the edge of the shell. The resultant structure is shown in FIGS. 13i and 13i'.

The wafer is then cleaned (step B) and approximately 0.4 μm of polysilicon is deposited (step M) to form a thin, protective layer over the electrical contacts during a subsequent HF etch. This results in the structure of FIGS. 13j and 13j'. The polysilicon is then patterned (step H), etched (step N), and the resist is stripped (step K). This results in the removal of the polysilicon that is not covering the circuitry, as shown in FIGS. 13k and 13k'.

The wafer is then cleaned (step B) and approximately 0.5 μm of silicon nitride is deposited (step D). The silicon nitride, shown in FIGS. 13L and 13L', is used as the masking material for the silicon isotropic etch. The silicon nitride is then patterned (step H), etched (step L), and the resist is stripped (step K). This results in the structure of FIGS. 13m and 13m'. The device is then submerged in isotropic silicon etchant (step O), producing the structure of FIGS. 13n and 13n'.

The wafer is then submerged in HF (step S), to remove most of the silicon nitride, release the probe, and to remove phosphosilicate glass. The resulting structure is shown in FIGS. 13o and 13o'. Some silicon nitride should remain to insulate the heaters from the substrate so timing of the HF etch is important. The wafer is then rinsed in deionized water-for approximately one hour.

A short silicon plasma etch (step N) is then performed to remove the thin, protective layer of polysilicon over the circuitry. This operation results in the device of FIGS. 13p and 13p'. The final step is a quick dip in hydroflouric acid to remove the oxide covering the polysilicon contacts (step Q). The final structure is shown in FIGS. 13q and 13q'.

EXAMPLE VI

Figure 14A:
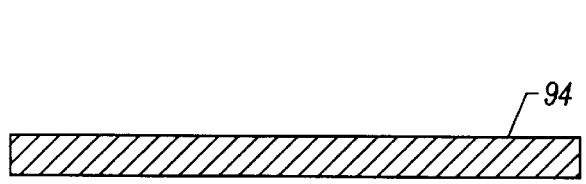
FIGS. 14a–14m' illustrate the construction of a probe in accordance with a sixth example of the invention.
Figure 14A:
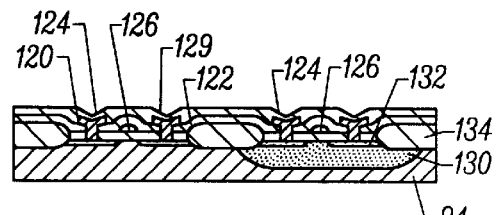

FIGS. 14a–14m' illustrate the process flow for an isotropically shaped probe incorporating an anisotropic etch to form a channel. The process utilizes a thin wafer with circuitry and double sided etching. In the following figures, the figures on the left-hand side of each page are cross-sections of the probe shaft, while the figures on the right-hand side of each page are cross-sections of the circuitry. FIG. 14a shows a (100) silicon p-type wafer that is approximately 100 μm thick. FIG. 14a' shows a structure of the type described in reference to FIG. 13a', but without layers 92 and 96 of FIG. 13a'.

Figure 14B:
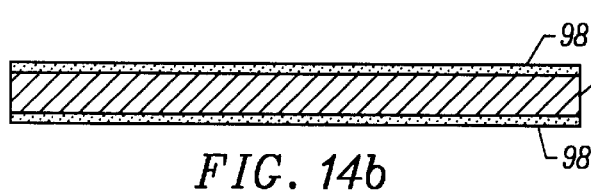
Figure 14B:
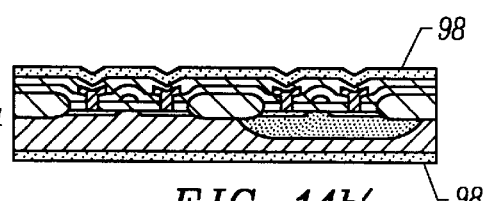
Figure 14C:
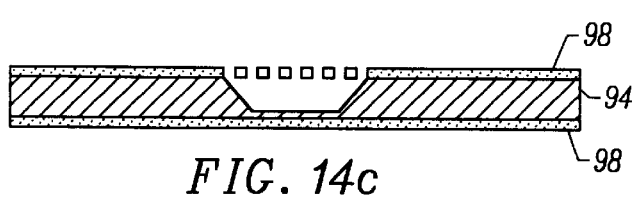
Figure 14C:

The wafer is cleaned (step B). Approximately 0.5 μm of silicon nitride is then deposited (step D). The resultant structure is shown in FIGS. 14b and 14b'. The silicon nitride is then patterned (step H), etched (step L), and the resist is stripped (step K). The single crystal silicon is then etched in an anisotropic etchant (step P) to form the trench for the fluid passage. The resultant structure is shown in FIGS. 14c and 14c'.

Figure 14D:
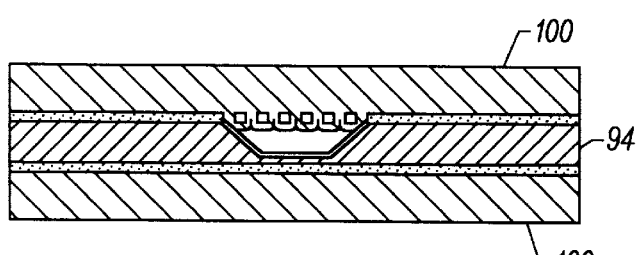
Figure 14D:
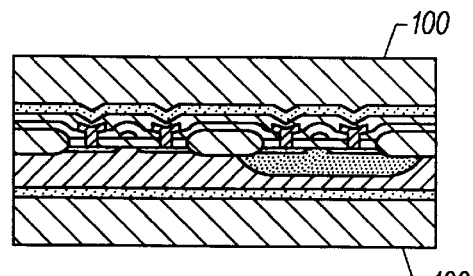
Figure 14E:
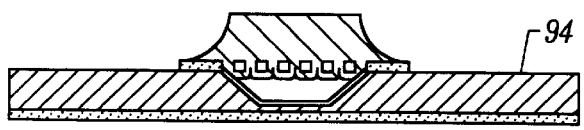
Figure 14E:
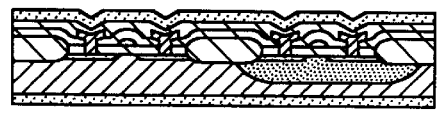

The wafer is then cleaned (step A) and approximately 2 μm of phosphosilicate glass is deposited (step E) to fill openings in the silicon nitride masking layer. The resultant structure is shown in FIGS. 14d and 14d'. The phosphosilicate glass is then patterned (step H), etched (step J), and the resist is stripped (step K). This results in the formation of a mold to make the fluid channel cap. The silicon nitride is then etched (step L). The resultant structure is shown in FIGS. 14e and 14e'. The resist can typically be removed before the nitride etch since the phosphosilicate glass acts as an etch mask. In some cases, the thickness of the phosphosilicate glass may not be thick enough to prevent the etch from attacking the underlying nitride, in which case photoresist may be necessary.

Figure 14F:
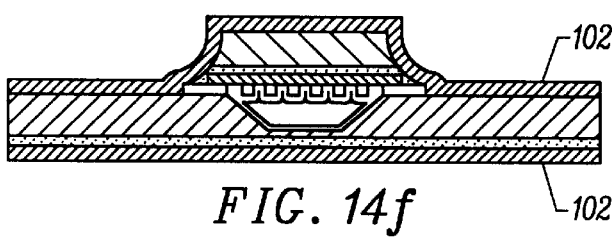
Figure 14F:
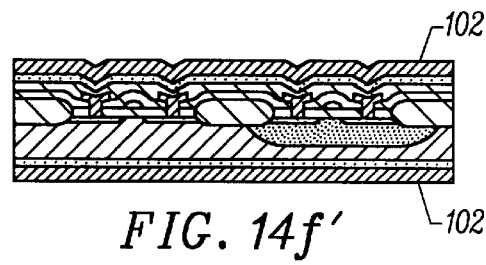
Figure 14G:
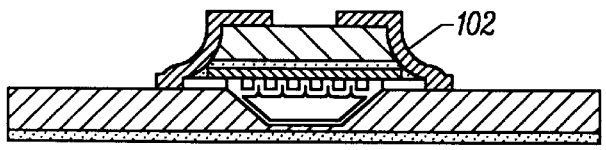
Figure 14G:
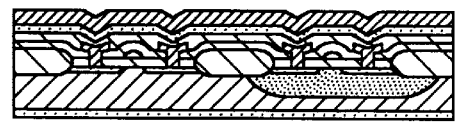

The wafer is then cleaned (step B) and approximately 2 μm of polysilicon is deposited (step M) to form the frame material of the fluid channel. The resultant structure is shown in FIGS. 14f and 14f'. The polysilicon is then patterned (step H) and etched (step N) to form the fluid inlet and outlet ports and to remove the polysilicon away from the edge of the shell. The polysilicon is then removed from the back side of the wafer (step N) and the resist is stripped (step K). The resultant structure is shown in FIGS. 14g and 14g'.

Figure 14H:
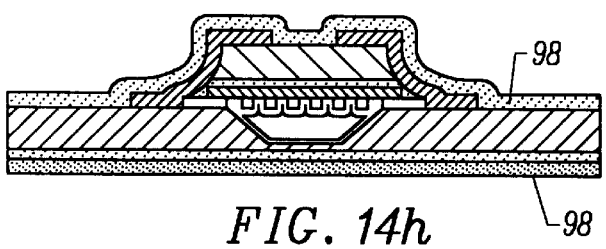
Figure 14H:
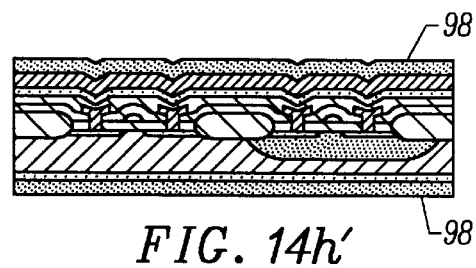
Figure 14I:
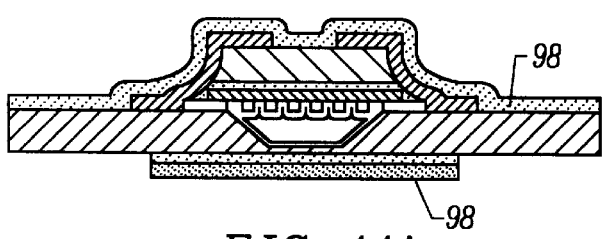
Figure 14I:
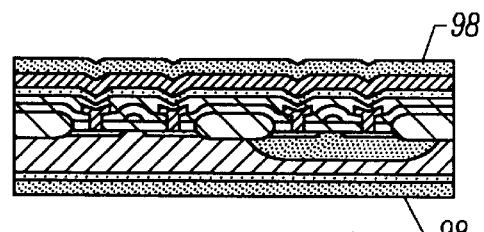
Figure 14J:
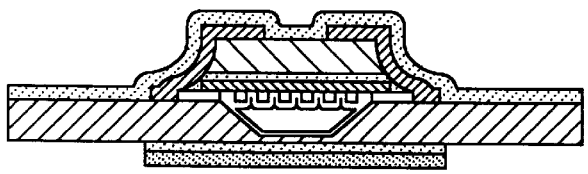
Figure 14J:
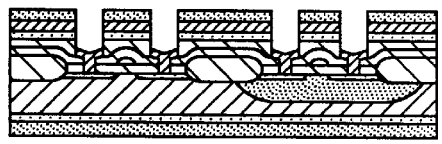

The wafer is then cleaned (step B) and approximately 0.5 μm of silicon nitride is deposited (step D) to function as a masking material for the silicon isotropic etch. FIGS. 14h and 14h' show the resultant structure. The silicon nitride is then patterned (step H), etched (step L), and the resist is stripped (step K), to generate the structure shown in FIGS. 14i and 14i'. The silicon nitride of the electrical contacts is then patterned (step H) and the silicon nitride layer is etched (step L), the polysilicon layer is etched (step N), the silicon nitride layer is etched (step L), and the oxide layer is etched (step Q), to expose the electrical contacts as shown in FIG. 14j'. The resist is then stripped (step K).

Figure 14K:
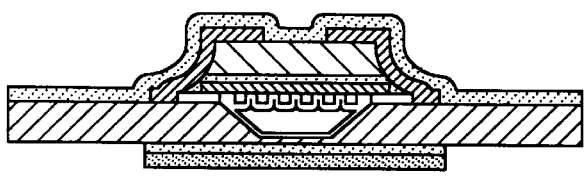
Figure 14K:
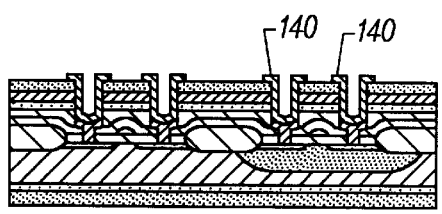
Figure 14L:
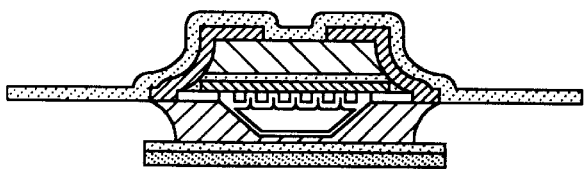
Figure 14L:
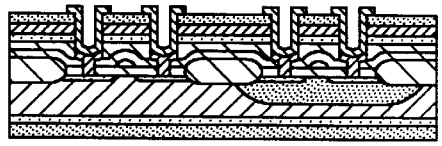
Figure 14M:
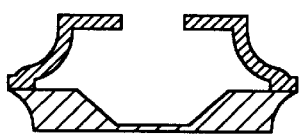
Figure 14M:
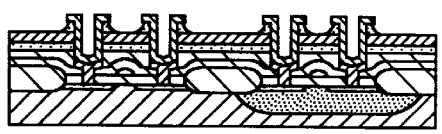

The wafer is then cleaned (step B) and gold is sputtered (step T) on the front side of the wafer. Preferably, a chromium adhesion layer is used. The gold is patterned (step H), etched (step U), and the resist is stripped (step K). The resultant gold pockets are shown in FIG. 14k'. The wafer is then submerged in an isotropic etchant (step O), producing the structure of FIGS. 14l and 14l'. The wafer is then submerged in HF (step S) to remove the silicon nitride, release the probe, and remove the phosphosilicate glass. The wafer is then rinsed in deionized water for approximately one hour to produce the structure shown in FIGS. 14m and 14m'.

EXAMPLE VII

Figure 15A:
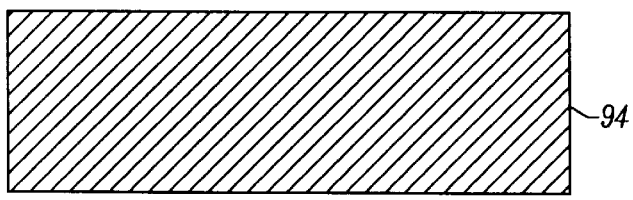
FIGS. 15a–15m' illustrate the construction of a probe in accordance with a seventh example of the invention.
Figure 15A:
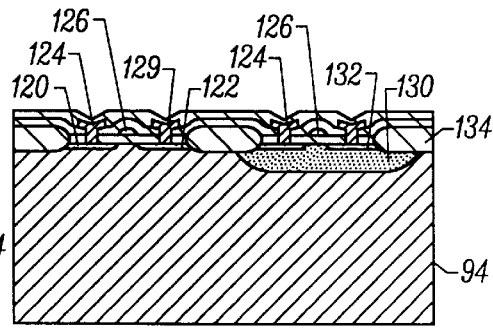

FIGS. 15a–15m' illustrate the process flow for an isotropically shaped probe incorporating an anisotropic etch to form a channel. The process utilizes a standard thickness wafer with circuitry and double sided etching. In the following figures, the figures on the left-hand side of each page are cross-sections of the probe shaft, while the figures on the right-hand side of each page are cross-sections of the circuitry. FIG. 15a shows a (100) silicon p-type wafer that is approximately 500 μm thick. FIG. 15a' shows a structure of the type described in reference to FIG. 13a', but without layers 92 and 96 of FIG. 13a'.

Figure 15B:
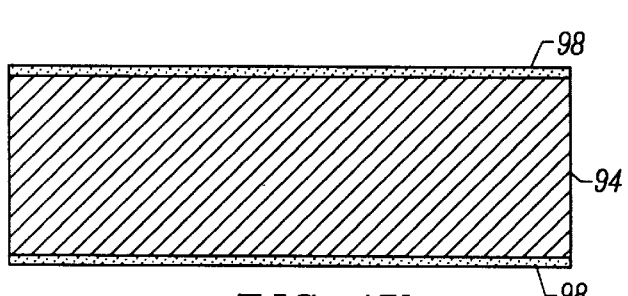
Figure 15B:
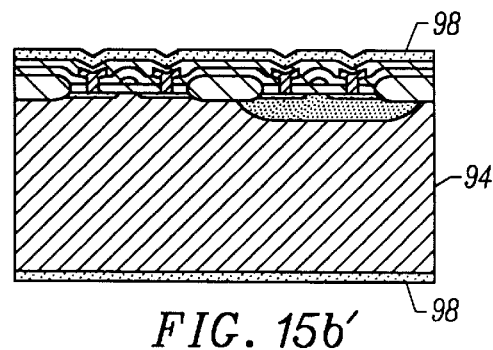
Figure 15C:
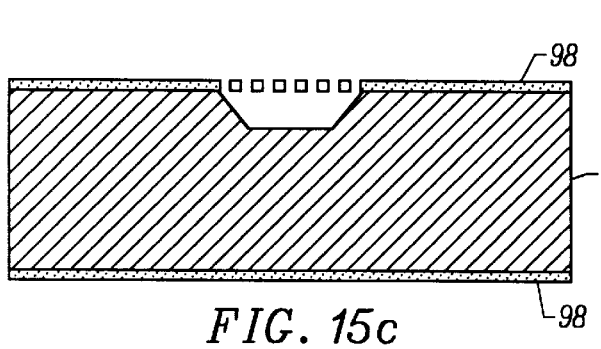
Figure 15C:
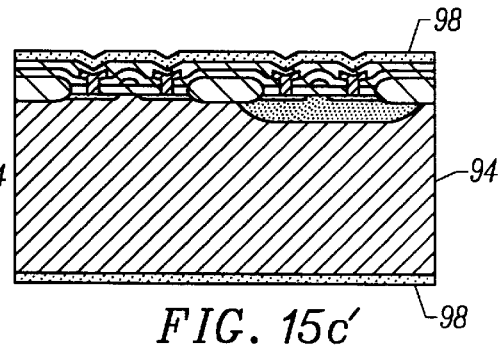

The wafer is cleaned (step B) and approximately 0.5 μm of silicon nitride is deposited (step D), resulting in the structure of FIGS. 15b and 15b'. The silicon nitride is then patterned (step H), etched (step L), and the resist is stripped (step K). The single crystal silicon is then etched in an anisotropic etchant (step P) to form a fluid passage trench, as shown in FIG. 15c.

Figure 15D:
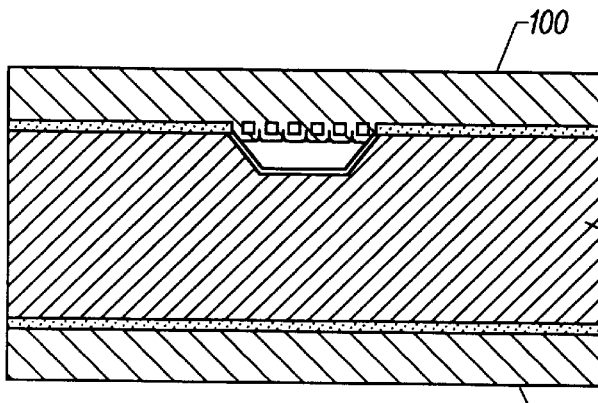
Figure 15D:
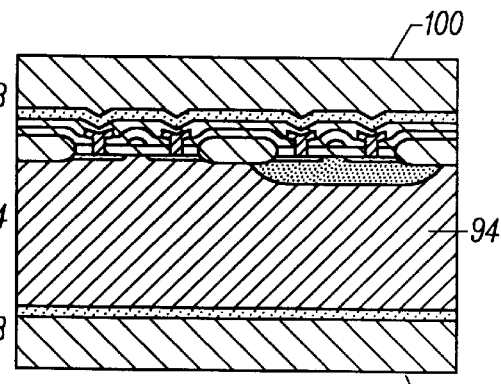
Figure 15E:
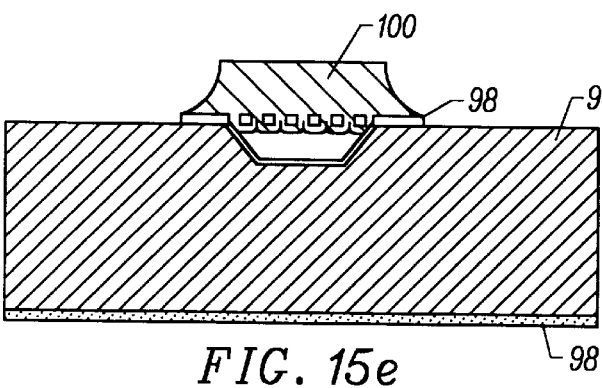
Figure 15E:
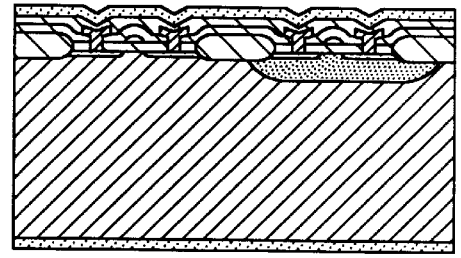

The wafer is then cleaned (step B) and approximately 2 μm of phosphosilicate glass is deposited (step E) to fill openings in the silicon nitride masking layer. The resultant structure is shown in FIGS. 15d and 15d'. The phosphosilicate glass is then patterned (step H), etched (step J), and the resist is stripped (step K). This forms the mold to make the fluid channel cap. The silicon nitride is then etched (step L), resulting in the structure shown in FIGS. 15e and 15e'. The resist can typically be removed before the nitride etch since the phosphosilicate glass acts as an etch mask. In some cases, the thickness of the phosphosilicate glass may not be thick enough to prevent the etch from attacking the underlying nitride in which case, photoresist may be necessary.

Figure 15F:
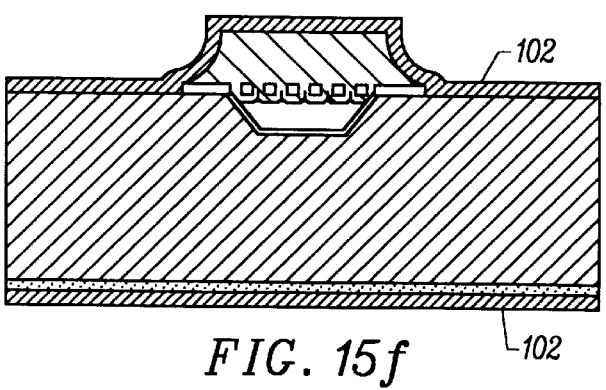
Figure 15F:
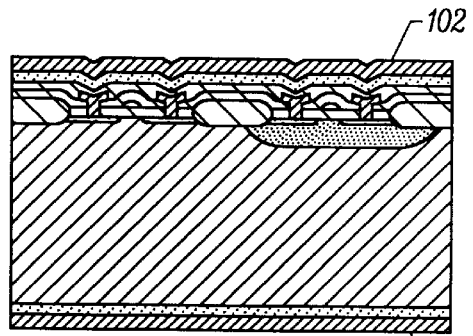
Figure 15G:
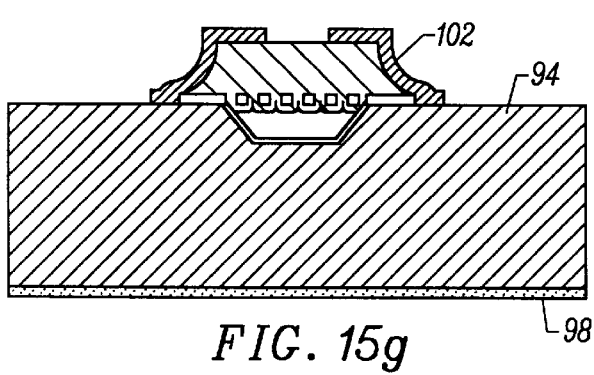
Figure 15G:
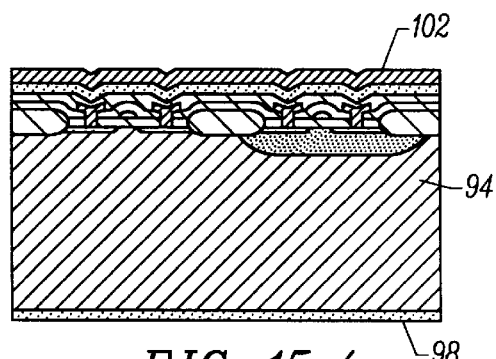

The wafer is then cleaned (step B) and approximately 2 μm of polysilicon is deposited (step M) to form the frame material, as shown in FIGS. 15f and 15f'. The polysilicon is then patterned (step H) and etched (step N) to form the channel cap inlet and outlet port, to remove the polysilicon away from the edge of the shell, and to remove polysilicon from the back side of the wafer (step N). The resist is then stripped (step K). The resultant structure is shown in FIGS. 15g and 15g'.

Figure 15H:
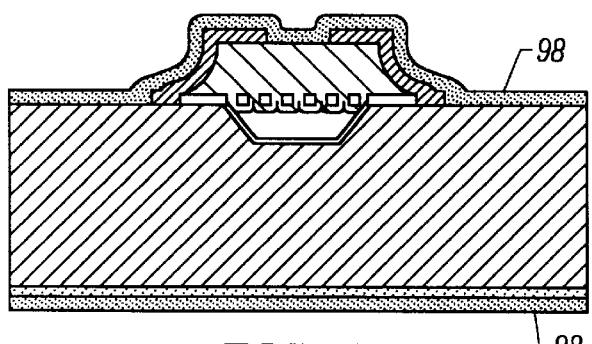
Figure 15H:
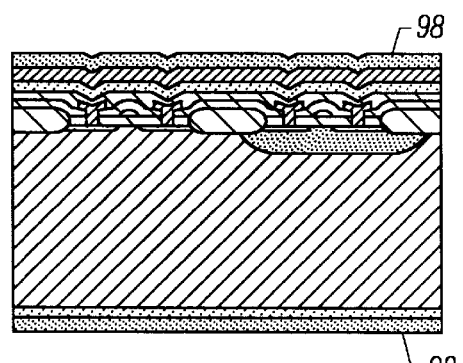
Figure 15I:
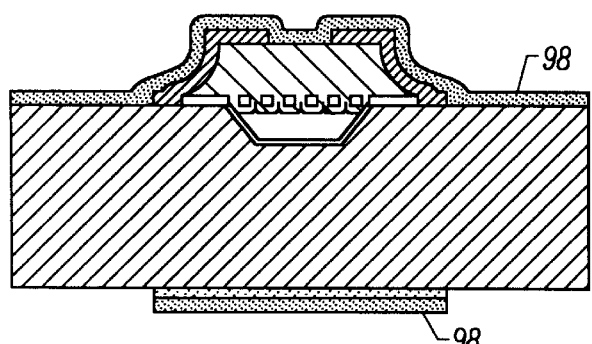
Figure 15I:
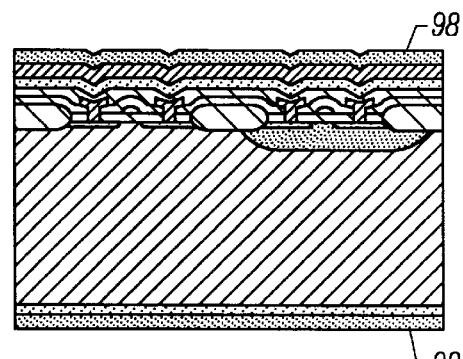

The wafer is then cleaned (step B) and approximately 0.5 μm of silicon nitride is deposited (step D). The silicon nitride serves as the masking material for the silicon isotropic etch. The silicon nitride layer is shown in FIGS. 15h and 15h'. The silicon nitride is patterned (step H), etched (step L), and the resist is stripped (step K). This results in the structure shown in FIGS. 15i and 15i'.

Figure 15J:
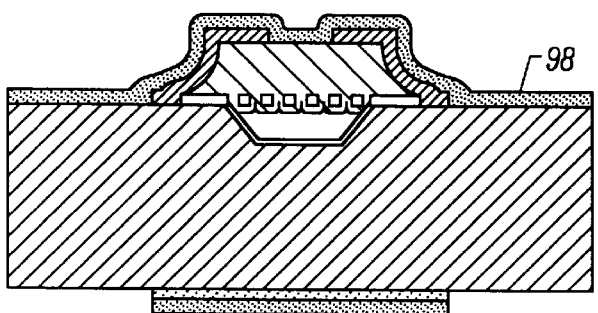
Figure 15J:
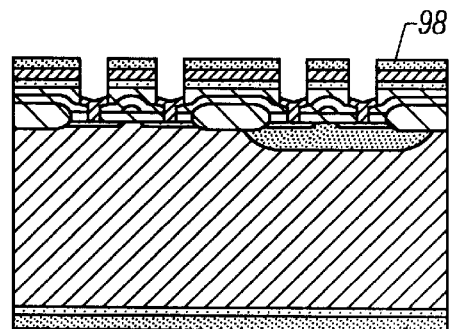
Figure 15K:
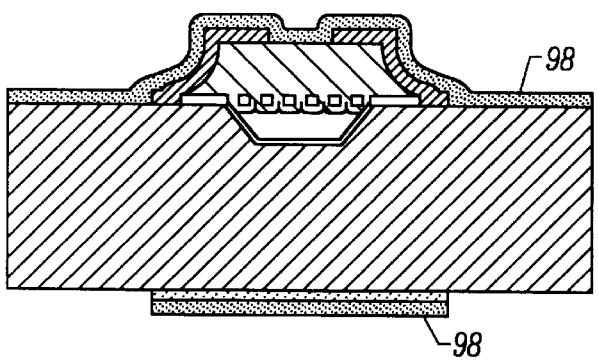
Figure 15K:
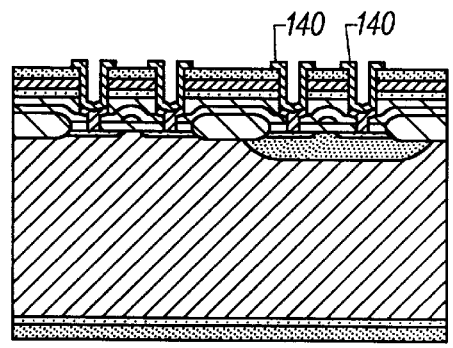

A pattern is then applied over the electrical contacts (step H). The silicon nitride layer is then etched (step L), the polysilicon layer is etched (step N), the silicon nitride layer is etched (step L), and the oxide layer is etched (step Q). The resist is then stripped (step K). The resultant structure is shown in FIGS. 15j and 15j'.

The wafer is then cleaned (step B) and gold is sputtered (step T) onto the front side of the wafer. The gold is patterned (step H), etched (step U), and the resist is stripped (step K), to yield the structure of FIGS. 15k and 15k'. Additional adhesion layers such as titanium or chromium may be necessary to be deposited before the gold deposition.

Figure 15L:
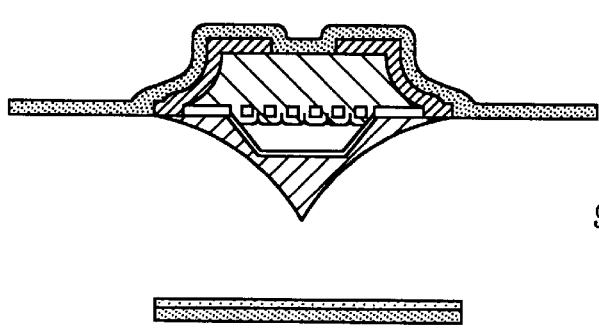
Figure 15L:
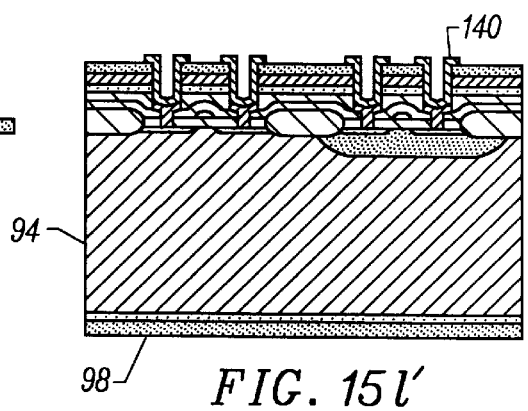
Figure 15M:
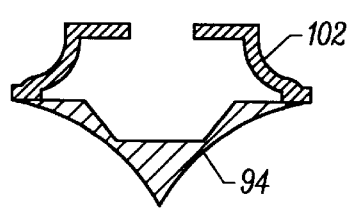
Figure 15M:
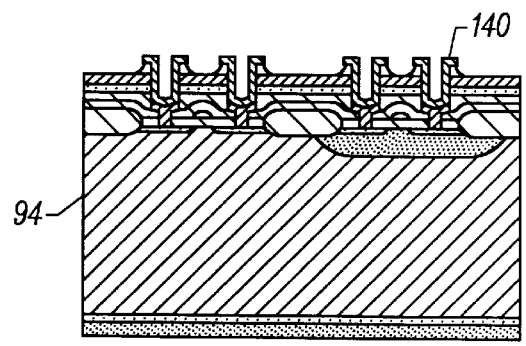

The wafer is then submerged in an isotropic silicon etchant (step O), to produce the structure of FIGS. 15l and 15l'. The wafer is then submerged in HF (step S) to remove silicon nitride, release the probe, and remove phosphosilicate glass. The wafer is then rinsed in deionized water for approximately one hour. The final structure is shown in FIGS. 15m and 15m'.

EXAMPLE VIII

FIGS. 16a–16o' illustrate the process flow for an anisotropically and isotropically shaped probe incorporating an anisotropic etch to form the channel. The device is fabricated on an SOI wafer with a (110) top layer. The processing is used to construct a device of the type shown in FIGS. 6–7. The figures on the left-hand side of the page show the cross-section of the tip region, while the figures on the right-hand side of the page show the cross-section of the probe shaft region.

FIGS. 16a and 16a' show a (110) silicon wafer bonded to oxide on a silicon wafer. The wafer is cleaned (step A) and approximately 0.5 μm of silicon nitride is deposited (step D), resulting in the device shown in FIGS. 16b and 16b'. The silicon nitride is then patterned (step H), etched (step L), and the resist is stripped (step K). The single crystal silicon is then subject to an anisotropic etchant (step P) to form the trench for the fluid passage, resulting in the device of FIGS. 16c and 16c'.

Figure 16E:
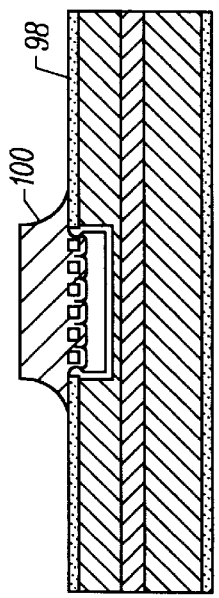
FIGS. 16a–16o' illustrate the construction of a probe in accordance with an eighth example of the invention.
Figure 16F:
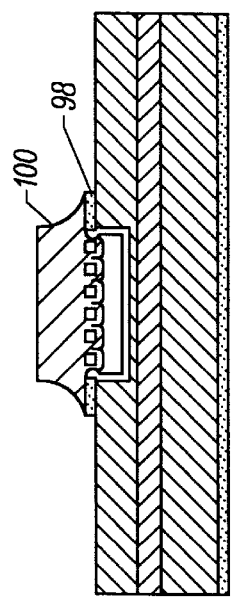

The wafer is then cleaned (step A) and approximately 2 μm of phosphosilicate glass is deposited (step E) to fill openings in the silicon nitride masking layer, as shown in FIGS. 16d and 16d'. The phosphosilicate glass is then patterned (step H), etched (step J), and the resist is stripped (step K). This operation exposes regions of the silicon nitride, as shown in FIGS. 16e and 16e'. The silicon nitride is then etched (step L) to produce the structure of FIGS. 16f and 16f'. The resist can typically be removed before the nitride etch since the phosphosilicate glass acts as an etch mask. In some cases, the thickness of the phosphosilicate glass may not be thick enough to prevent the etch from attacking the underlying nitride, in which case photoresist may be necessary.

Figure 16G:
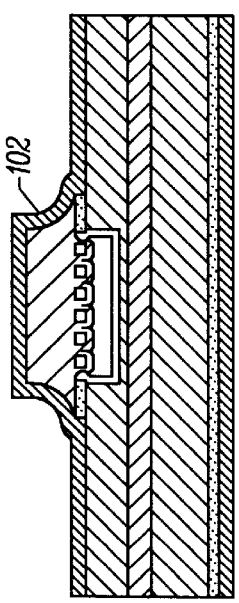
Figure 16E:
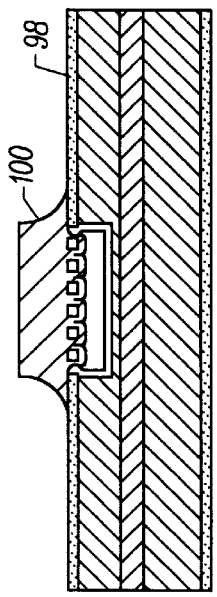
Figure 16F:
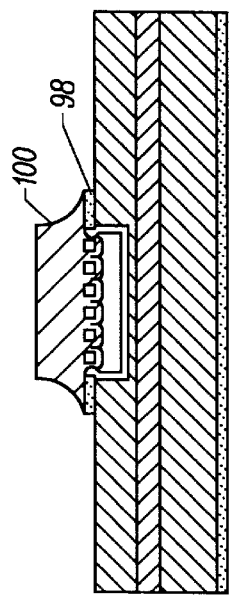
Figure 16G:
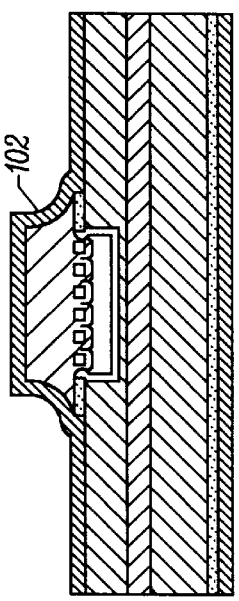

The wafer is then cleaned (step B) and approximately 2 μm of polysilicon is deposited (step M) to form the frame material of the fluid channel. The resultant structure is shown in FIGS. 16g and 16g'. The polysilicon is then patterned (step H) and etched (step N) to form the channel cap inlet and outlet ports. The resist is then stripped (step K). This results in the device of FIGS. 16h and 16h'.

The wafer is then cleaned (step B) and approximately 0.5 μm of silicon nitride (step D) is deposited, as shown in FIGS. 16i and 16i'. The silicon nitride operates as the masking material for the silicon isotropic etch. The silicon nitride is patterned (step H), etched (step L), and the resist is stripped (step K). This results in the structure of FIGS. 16j and 16j'.

Figure 16K:
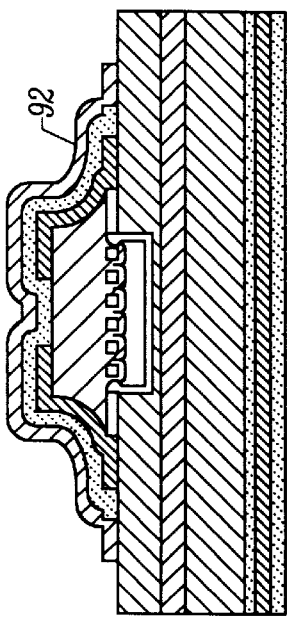

The wafer is then cleaned (step A) and approximately 2 μm of low temperature oxide (step F) is deposited for the anisotropic etch masking material. An alternative masking material is polyhexane or even an additional layer of silicon nitride. The deposited substance is patterned (step H), etched (step J), and the resist is stripped (step K) to yield the structure of FIGS. 16k and 16k'.

Figure 16L:
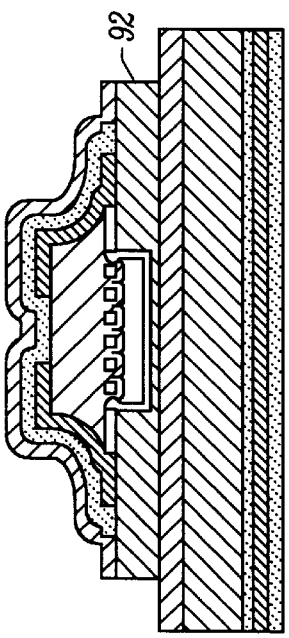
Figure 16M:
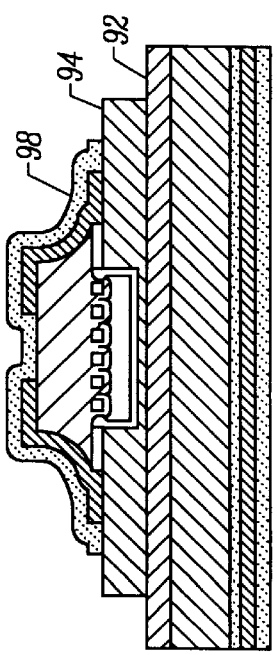
Figure 16K:
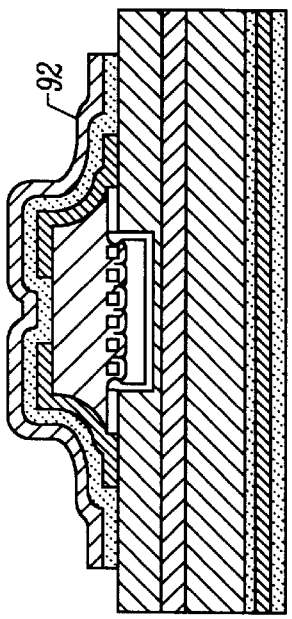
Figure 16L:
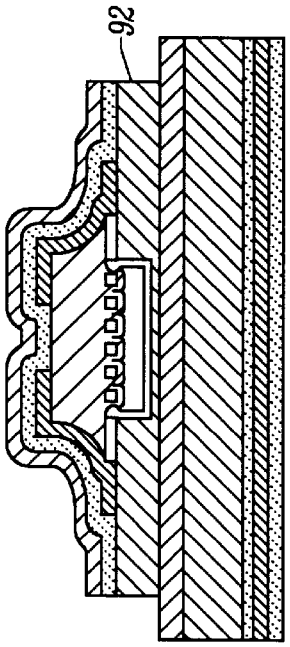
Figure 16M:
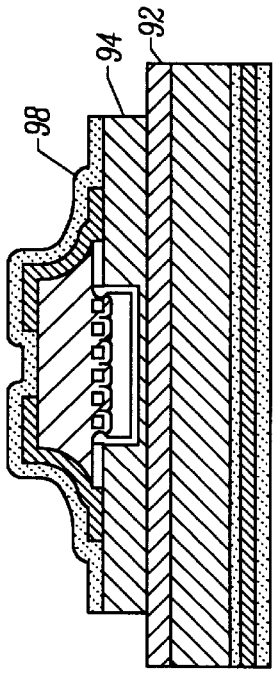

The single crystal silicon is then etched in an anisotropic etchant (step P) to form vertical walls along the shaft of the probe, as shown in FIGS. 16l and 16l'. The low temperature oxide anisotropic silicon etchant mask is then removed (step Q), to generate the structure of FIGS. 16m and 16m'.

The wafer is then submerged in an isotropic silicon etchant (step O) to produce smooth, converging surfaces at the tip, as shown in FIG. 16n. The wafer is then submerged in HF (step S) to remove silicon nitride, release the probe, and remove the phosphosilicate glass, as shown in FIGS. 16o and 16o'. The wafer is then rinsed in deionized water for approximately one hour.

The techniques of the invention may also be used in connection with non-SOI, standard thickness wafers. The expense of SOI wafers and thin wafers is approximately four times that of standard wafers. Therefore, it is desirable to use standard wafers, yet retain the geometry control provided by SOI and thin wafers. Standard thickness wafer processing discussed below does not apply to double sided etched devices of the type described above.

The processing of standard thickness, non-SOI wafers involves a grind step and a chemical mechanical polish. FIG. 17 illustrates a basic process flow. FIG. 18 illustrates an alternate process flow with an additional step. The additional step is an oxidation that assists in the chemical mechanical polishing process by providing an etch stop. Having an etch stop improves the uniformity of the shapes of the probes. A third process flow is shown in FIG. 19. This process flow has an additional step of a temporary bond to a plain, standard wafer. The purpose of the bond is to rigidly fix the probes during the grinding and polishing steps. There is a possibility that during the grinding and polishing steps that the probes may not be held sufficiently tight using only adhesives and that a stronger bond, like that supplied by an oxide to oxide fusion bond, may be necessary. Otherwise, if the probes were to move during the grinding and polishing steps, their sharpness may be decreased. The standard wafer used for the temporary fusion bond should be able to be reused many times. Therefore, it does not add significant cost.

EXAMPLE IX

Figure 17A:
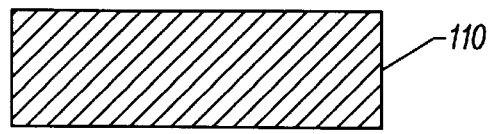
FIGS. 17a–17f illustrates the construction of a probe in accordance with a ninth example of the invention.
Figure 17B:
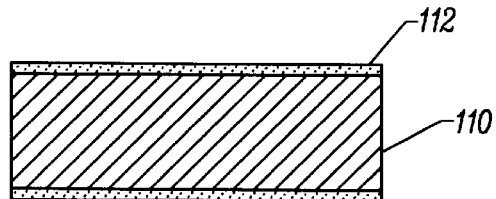

A single crystal (100) silicon p-type wafer approximately 500 μm thick is used as a starting wafer 110, as shown in FIG. 17(a). The wafer is cleaned (step A) and approximately 0.5 μm of silicon nitride (step D) is deposited. The deposited silicon nitride 112 is shown in FIG. 17(b). The silicon nitride is used as the masking material for the silicon isotropic etch.

Figure 17C:
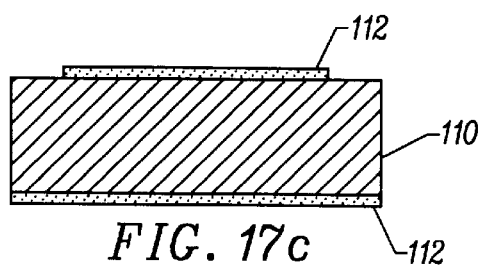
Figure 17D:
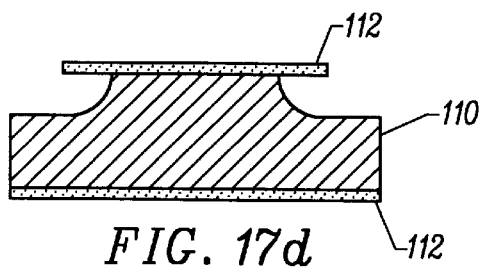
Figure 17E:
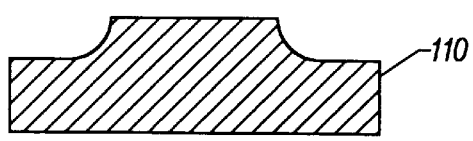
Figure 17F:
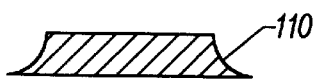

The silicon nitride is then patterned (step H), etched (step L), and the resist is stripped (step K), producing the device of FIG. 17(c). The wafer is then submerged in an isotropic silicon etchant (step O), producing the device of FIG. 17(d). The wafer is then submerged in HF (step S) to remove the silicon nitride, resulting in the device of FIG. 17(e). The wafer is then rinsed in deionized water for approximately 15 minutes. The majority of the silicon wafer is then grinded off to within a few micrometers of the bottom of the etched region. Then, using chemical mechanical polishing, the bottom of the wafer is polished until sharp structures are formed. The final device is shown in FIG. 17(f).

EXAMPLE X

Figure 18A:
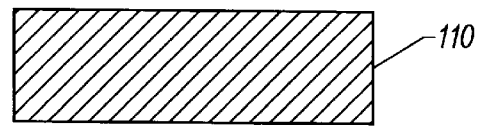
FIGS. 18a–18h illustrate the construction of a probe in accordance with a tenth example of the invention.
Figure 18B:
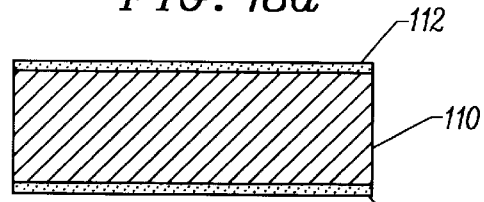

A single crystal (100) silicon p-type wafer approximately 500 μm thick is used as a starting wafer 110, as shown in FIG. 18(a). The wafer is cleaned (step A) and approximately 0.5 μm of silicon nitride (step D) is deposited. The deposited silicon nitride 112 is shown in FIG. 18(b). The silicon nitride is used as the masking material for the silicon isotropic etch.

Figure 18C:
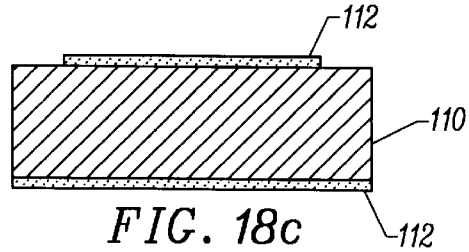
Figure 18D:
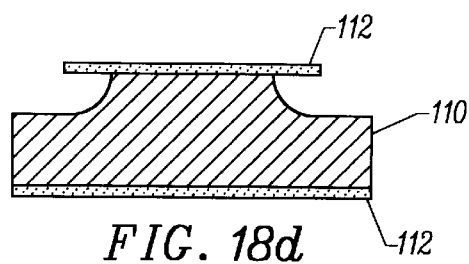
Figure 18E:
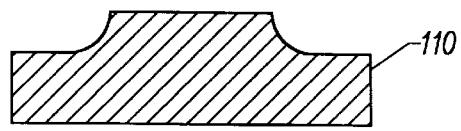

The silicon nitride is then patterned (step H), etched (step L), and the resist is stripped (step K), producing the device of FIG. 18(c). The wafer is then submerged in an isotropic silicon etchant (step O), producing the device of FIG. 18(d). The wafer is then submerged in HF (step S) to remove the silicon nitride, resulting in the device of FIG. 18(e).

Figure 18F:
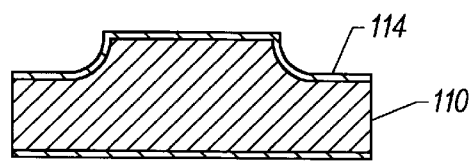
Figure 18G:
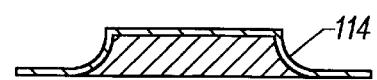

The wafer is then cleaned (step A) and a 1 μm thick layer of $SiO_2$ is thermally grown (step Y). The oxide layer 114 is shown in FIG. 18(f). The majority of the silicon wafer is then grinded off to within a few micrometers of the bottom of the etched region. Then, using chemical mechanical polishing, the bottom of the wafer is polished until sharp structures are formed. The resultant device is shown in FIG. 18(g). The wafer is then submerged in HF (step S) to remove the oxide.

Figure 18H:

The wafer is finally rinsed in deionized water for approximately 15 minutes, resulting in the device of FIG. 18(h).

EXAMPLE XI

Figure 19A:
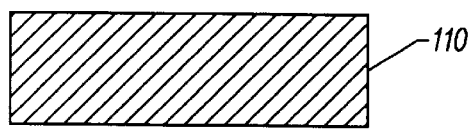
FIGS. 19a–19i illustrate the construction of a probe in accordance with an eleventh example of the invention.
Figure 19B:
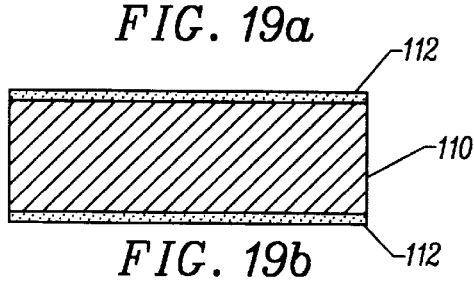

A single crystal (100) silicon p-type wafer approximately 500 μm thick is used as a starting wafer 10, as shown in FIG. 19(a). The wafer is cleaned (step B) and approximately 0.5 μm of silicon nitride (step D) is deposited. The deposited silicon nitride 112 is shown in FIG. 19(b). The silicon nitride is used as the masking material for the silicon isotropic etch.

Figure 19C:
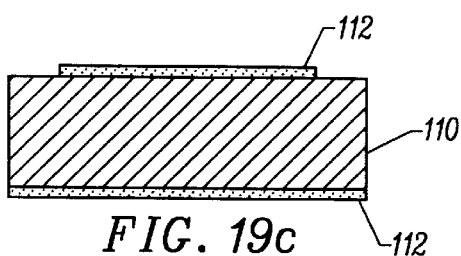
Figure 19D:
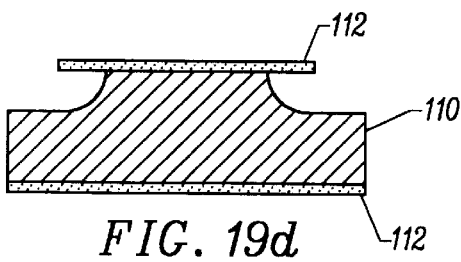
Figure 19E:
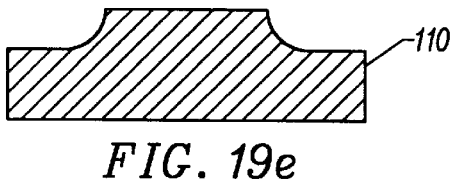
Figure 19F:
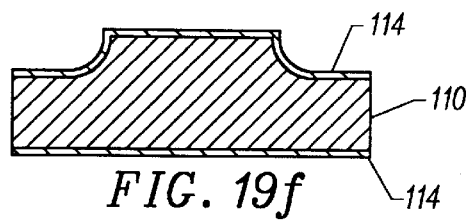

The silicon nitride is then patterned (step H), etched (step L), and the resist is stripped (step K), producing the device of FIG. 19(c). The wafer is then submerged in an isotropic silicon etchant (step O), producing the device of FIG. 19(d). The wafer is then submerged in HF (step S) to remove the silicon nitride, resulting in the device of FIG. 19(e). The wafer is then cleaned (step A) and a 1 μm thick layer of $SiO_2$ is thermally grown (step Y). The oxide layer 114 is shown in FIG. 19(f).

Figure 19G:
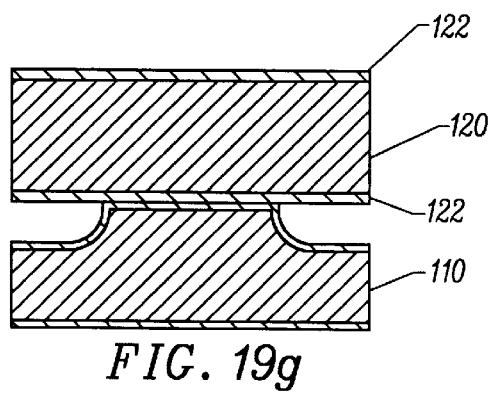
Figure 19H:
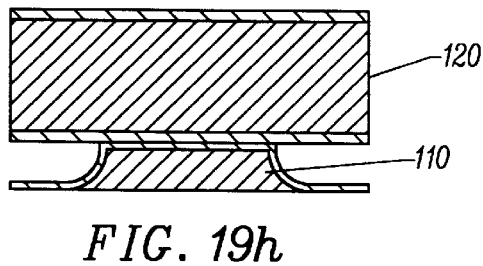
Figure 19I:
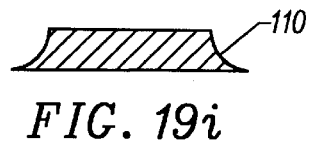

At this point, the thermally oxidized wafer 110 is bonded (step Z) to a standard, plain thermally oxidized wafer that has an approximately 1 μm thick layer of $SiO_2$ thermally grown thereon (step Y). FIG. 19(g) illustrates the wafer 110 bonded to a handle wafer 120, which has oxide layer 122. The wafer 110 is then grinded to within a few micrometers of the bottom of the etched region. The wafer is then chemical mechanically polished until sharp structures are formed. The resultant device is shown in FIG. 19(h). The wafer is then submerged in HF (step S) to remove the oxide and the handle wafer. The wafer is then rinsed in deionized water for approximately 15 minutes, resulting in the device of FIG. 19(i).

Example XII

In one embodiment of the invention, the shape of the tip is controlled through adjustments in the deposition conditions of a layer of phosphosilicate glass, which is sandwiched between a silicon nitride masking layer and the SOI device layer. By incorporating a layer of phosphosilicate glass between the masking layer and the single crystal silicon, the tip geometry can be controlled by changing the phosphorous doping of the phosphosilicate glass. The phosphosilicate glass can be used to prevent unwanted tip hooking.

Figure 20G:
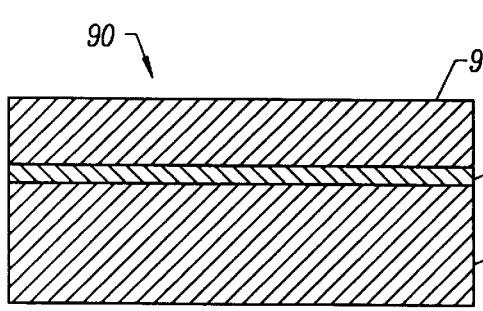
FIGS. 20a–20f illustrates the construction of a probe in accordance with a twelfth example of the invention.

FIG. 20(a) illustrates an SOI wafer 90 including an insulator layer 92 sandwiched between a device wafer 94 and a handle wafer 96. The device 94 is formed of single crystal silicon with a thickness of approximately 100 μm. The orientation is (100) or (110). The insulator 92 is thermally grown $SiO_2$, which is 1 to 2 μm thick, but may also be silicon nitride and/or chemically deposited oxide. The handle wafer 96 is 500 μm thick single crystal silicon with a (100) orientation.

Figure 20D:
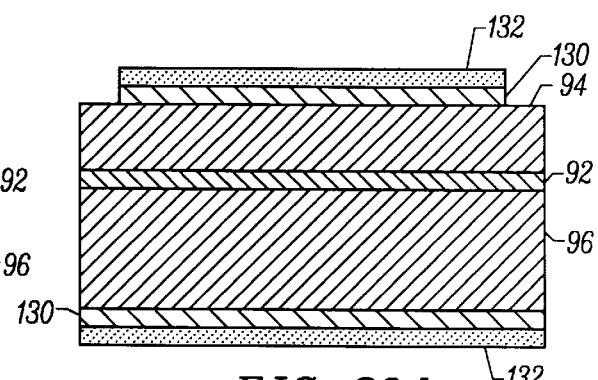
Figure 20B:
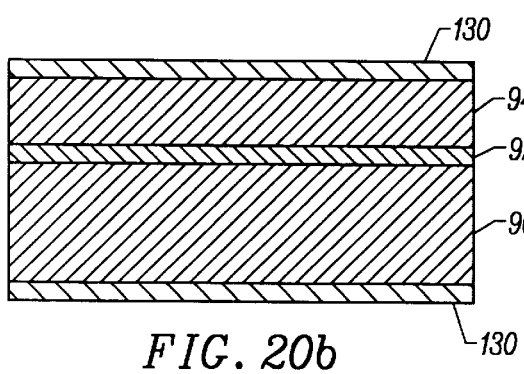
Figure 20E:
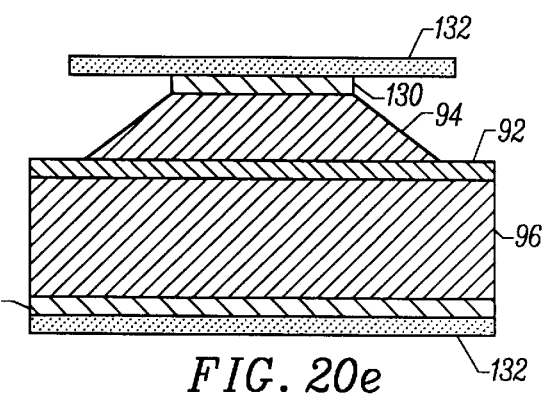
Figure 20C:
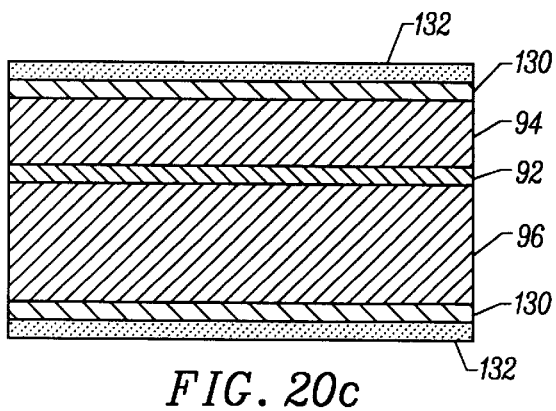

Approximately 800 nanometers of phosphosilicate glass is deposited (step E) on the wafer. FIG. 20(b) illustrates the phosphosilicate glass layer 130. Low-stress silicon nitride is then deposited on the wafer (step D). FIG. 20(c) illustrates the deposited layer 132.

Figure 20F:
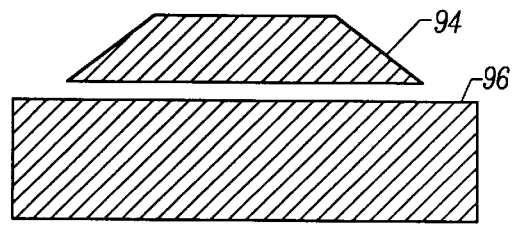

The silicon nitride layer 132 is then patterned (step H). Afterwards, the silicon nitride layer is etched (step L) and the phosphosilicate glass layer is etched (step J). This results in the device of FIG. 20(d). The silicon is then wet etched (step O), producing the device of FIG. 20(e). Finally, an HF release is performed (step S), producing the released device shown in FIG. 20(f).

The PSG reduces the incidence of tip hooks being formed. The tip hook problem occurs when the probe shape etch mask of low-stress silicon nitride is deposited directly onto silicon. The PSG placed between the silicon nitride and the silicon etches faster than the silicon. This faster etching material erodes during the etching process and therefore solves the silicon hooking problem.

Figure 21:
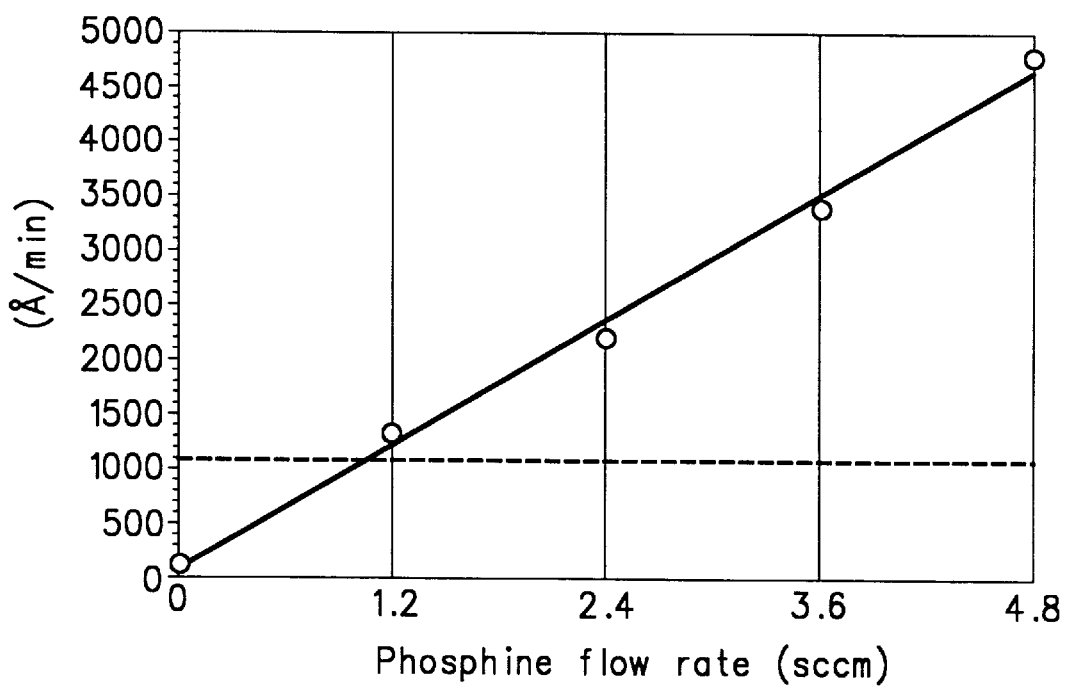
FIG. 21 illustrates isotropic etchant etch rate of PSG deposited using various phosphine flow rate parameters in accordance with the invention.

The etch rate of PSG was measured for a variety of phosphine flow rates. The etch rate results for wafers with PSG having $PH_3$ flow rates of 0.0, 1.2, 2.4, 3.6, and 4.8 sccm are shown in FIG. 21. Also shown in FIG. 21 is a horizontal line at 1100 Å/min which was the etch rate found for single crystal silicon. Based on the measured etch rates, PSG is a highly desirable material to correct the hooking problem, since its etch rate ratio to silicon can be tailored to be from 0.1 to over 4.3.

Figure 22A:
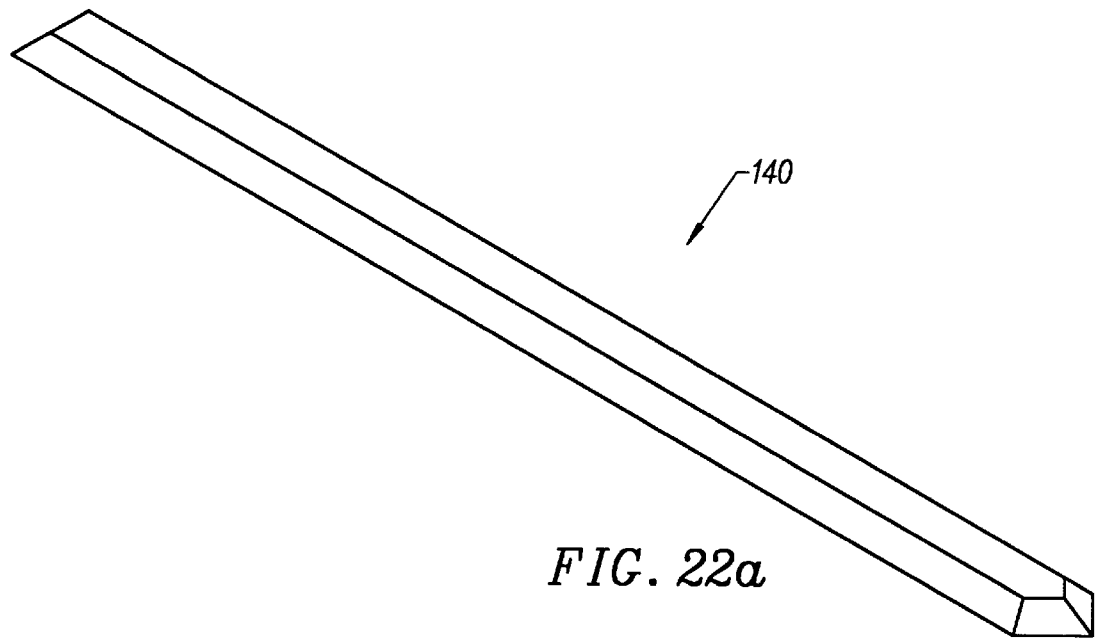
FIGS. 22a and 22b are perspective views of lancets constructed in accordance with the invention.
Figure 22B:
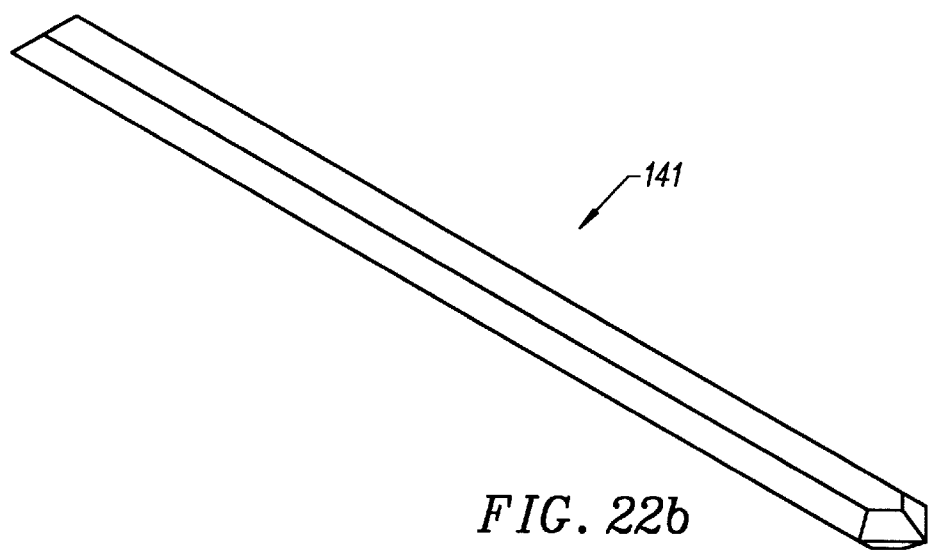

FIGS. 22A and 22B illustrate probes 140 and 141 constructed in accordance with any number of the example processes described herein. The probes do not include a channel and therefore are considered to be lancets or blades. The probes may be connected to larger structures to facilitate their use as lancets or blades. The probe 140 of FIG. 22A has an isotropically etched tip formed on one side of the device, while the probe 141 of FIG. 22B has an isotropically etched tip formed on both sides of the device.

Figure 23:
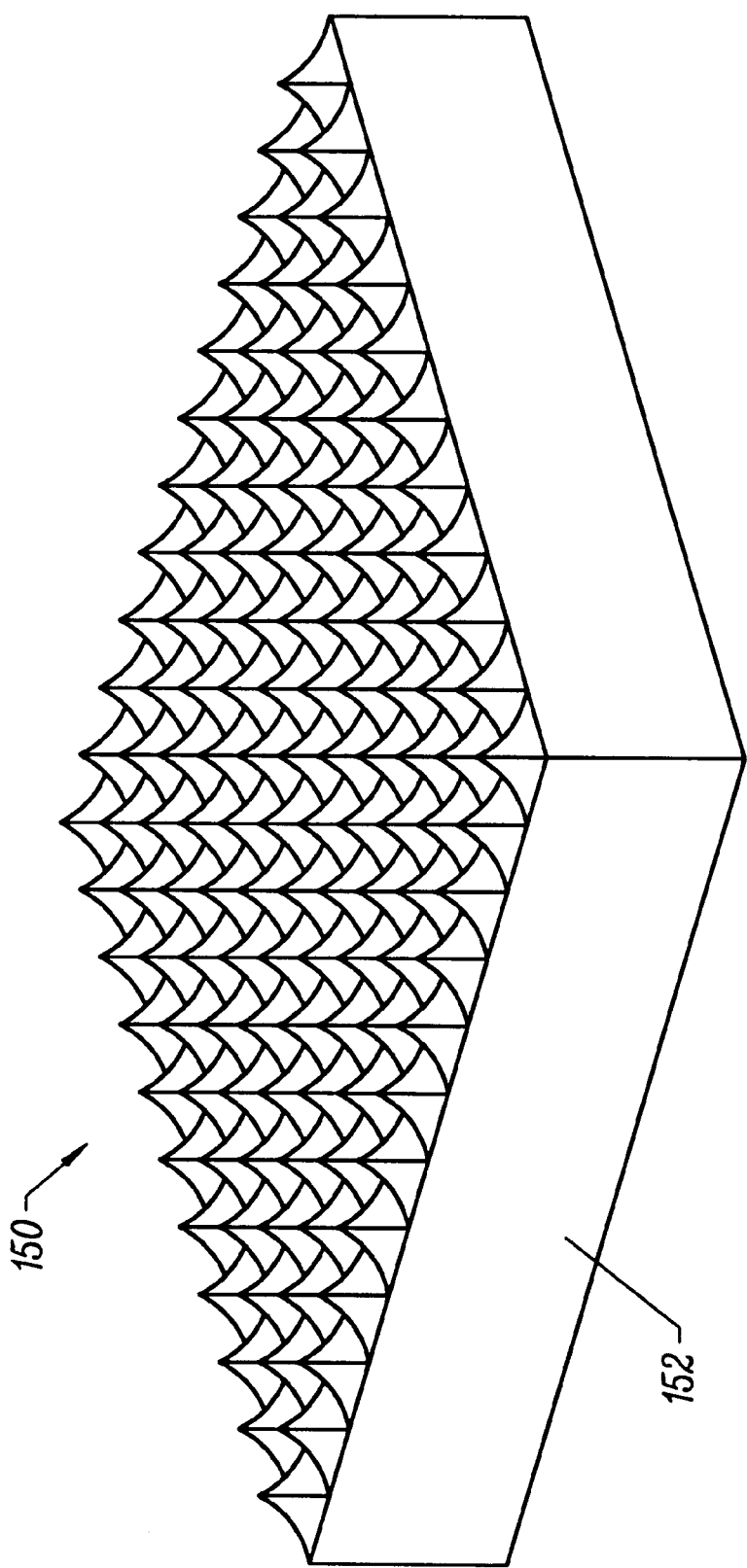
FIG. 23 illustrates an abrader constructed in accordance with an embodiment of the invention.
Figure 24:
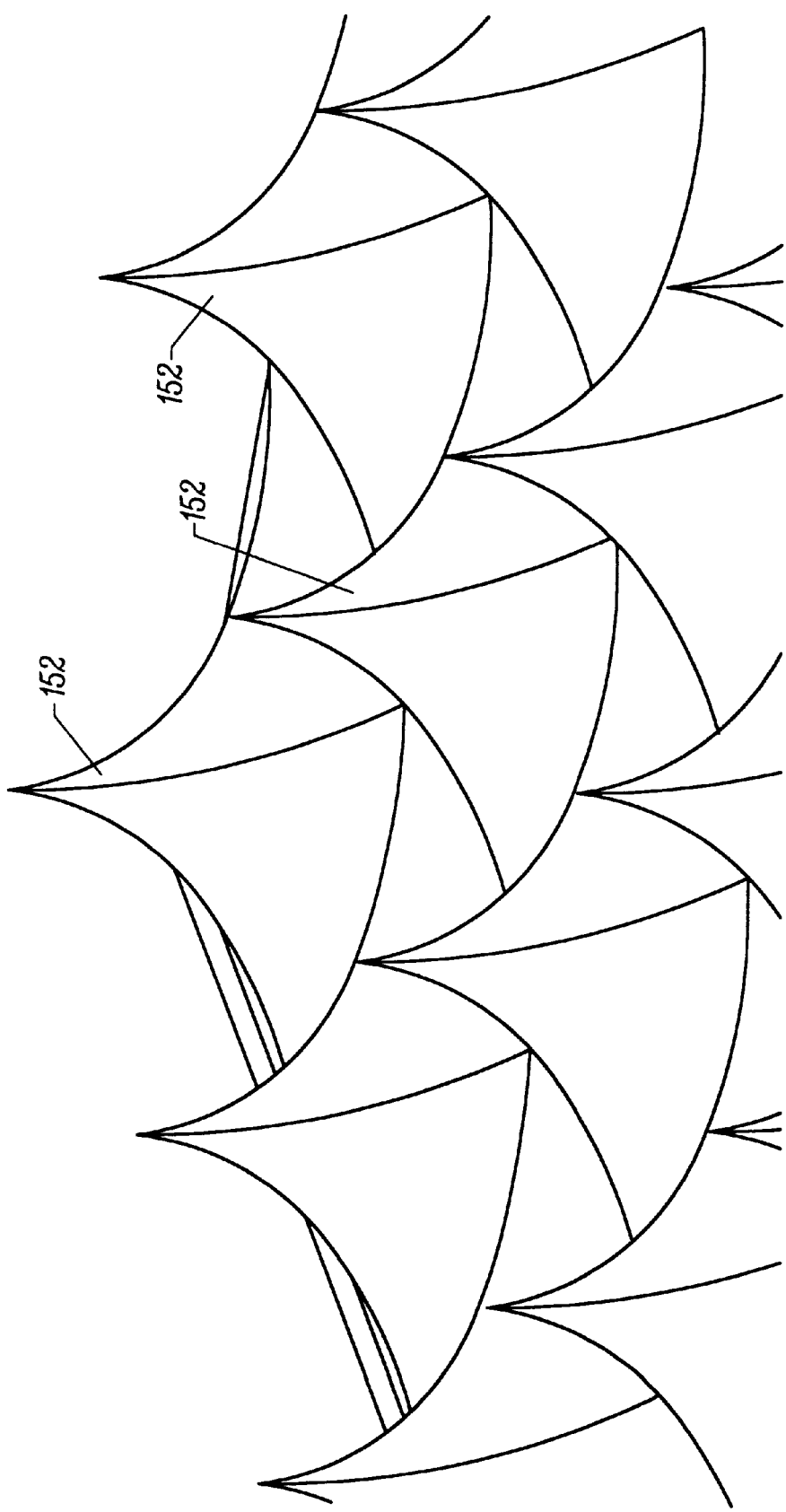
FIG. 24 is an enlarged view of isotropically etched tips associated with the abrader of FIG. 23.

FIG. 23 illustrates a matrix of isotropically etched tips constructed in accordance with an embodiment of the invention. The matrix 150 is formed on a semiconductor substrate 152. More particularly, the matrix 150 is formed on a planar surface of the substrate 152. The device 150 may be used as an "abrader". That is, the device may be used to abrade the epidermis to facilitate transdermal drug delivery. FIG. 24 is an enlarged view of individual isotropically etched tips 154 of the matrix 150. The tips have typical heights from 20 μm to 350 μm. The minimum spacing between the points is determined by their height. Typical spacings are between two times the height to over ten times the height. All of the points are fabricated using standard wafers. Three process are discussed below. The first process results in devices with sharp points. In some cases, these sharp points can break during use due to the small cross-section at the tips. Hence, two other processes are included to form arrays having duller points which are more durable. The first alternative process is accomplished by simply stopping the isotropic etch prematurely. The resulting structures have a flat-top rather than a point. The second alternative process is accomplished by the addition of a PSG layer between the silicon nitride masking layer. The resulting structures have a pyramid-like shape.

EXAMPLE XIII

Figure 25A:
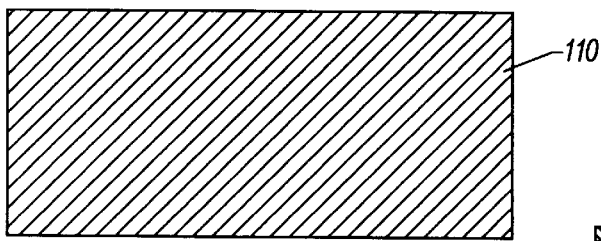
FIG. 25a–e illustrates the construction of an abrader with sharp tips in accordance with a thirteenth example of the invention.
Figure 25B:
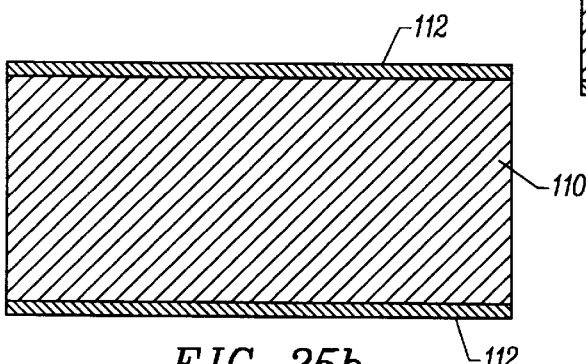

A single crystal (100) silicon wafer approximately 500 μm thick is used as a starting wafer 110, as shown in FIG. 25(a). The wafer is cleaned (step B) and approximately 0.5 μm of silicon nitride (step D) is deposited. The deposited silicon nitride 112 is shown in FIG. 25(b). The silicon nitride is used as the masking material for the silicon isotropic etch.

Figure 25C:
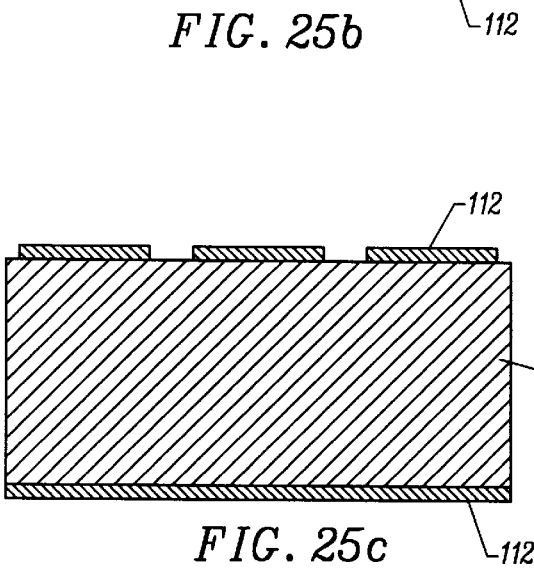
Figure 25D:
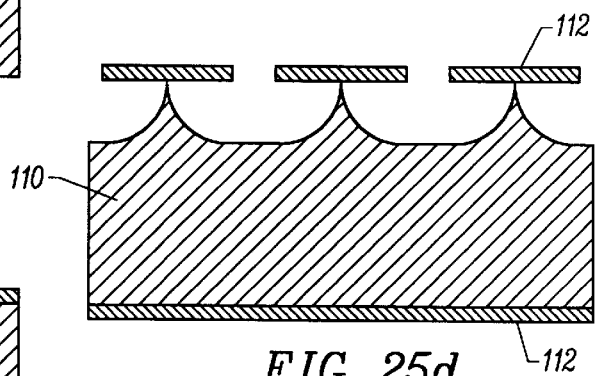
Figure 25E:
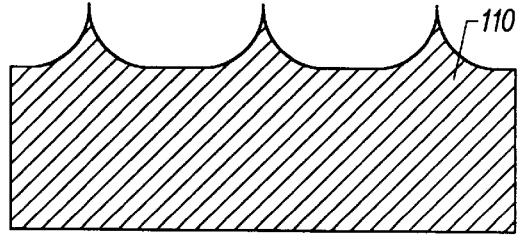

The silicon nitride is then patterned (step H), etched (step L), and the resist is stripped (step K), producing the device of FIG. 25(c). The wafer is then submerged in an isotropic silicon etchant (step O) until sharp points are formed, as shown in FIG. 25(d). The wafer is then rinsed in deionized water for approximately 15 minutes. Afterwards, the wafer is submerged in HF (step S) to remove the silicon nitride. Finally, the wafer is rinsed in deionized water for approximately 15 minutes, producing the device shown in FIG. 25(e).

EXAMPLE XIV

Figure 26A:
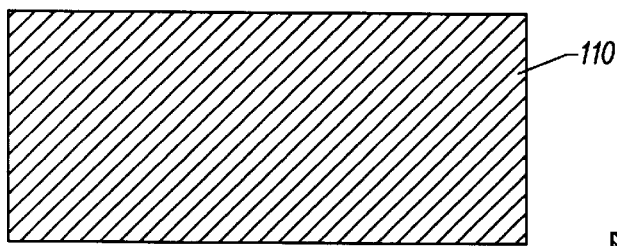
FIG. 26a–e illustrates the construction of an abrader with flat tips in accordance with a fourteenth example of the invention.
Figure 26D:
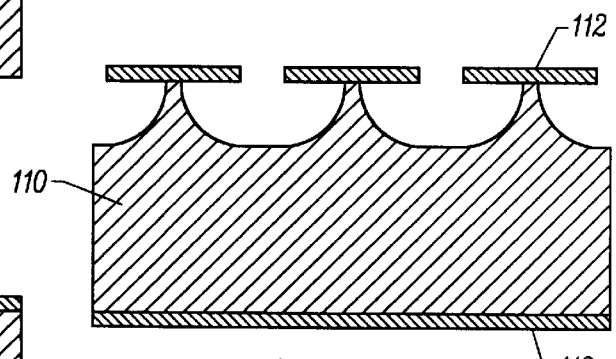
Figure 26B:
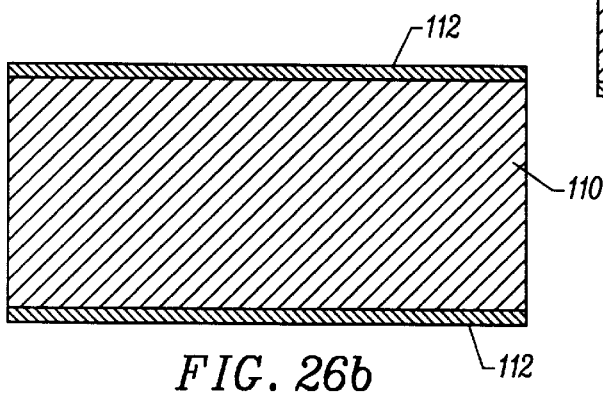

A single crystal (100) silicon wafer approximately 500 μm thick is used as a starting wafer 110, as shown in FIG. 26(a). The wafer is cleaned (step B) and approximately 0.5 μm of silicon nitride (step D) is deposited. The deposited silicon nitride 112 is shown in FIG. 26(b). The silicon nitride is used as the masking material for the silicon isotropic etch.

Figure 26E:
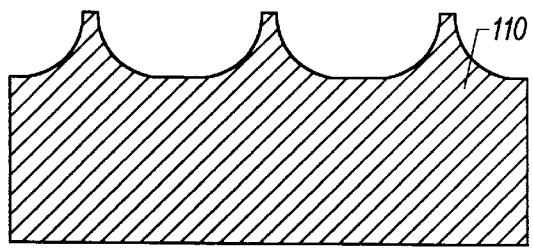
Figure 26C:
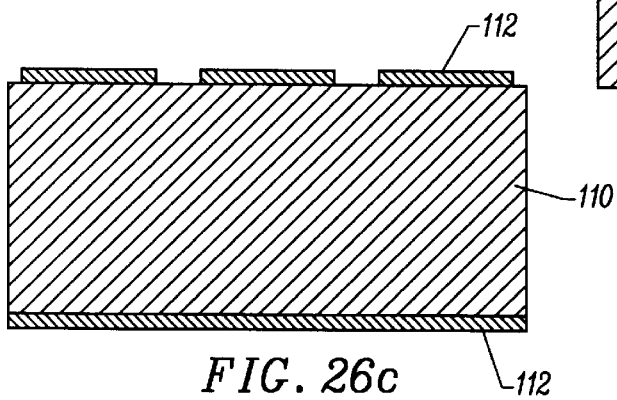

The silicon nitride is then patterned (step H), etched (step L), and the resist is stripped (step K), producing the device of FIG. 26(c). The wafer is then submerged in an isotropic silicon etchant (step O) and is subsequently removed before sharp points are formed. This processing results in the device of FIG. 26(d). The wafer is then rinsed in deionized water for approximately 15 minutes. Afterwards, the wafer is submerged in HF (step S) to remove the silicon nitride. Finally, the wafer is rinsed in deionized water for approximately 15 minutes, producing the device shown in FIG. 26(e).

EXAMPLE XV

Figure 27A:
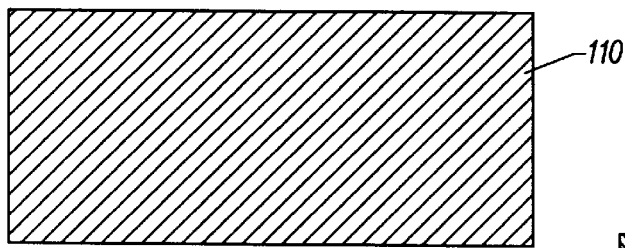
FIG. 27a–e illustrates the construction of an abrader with pyramidal projections in accordance with a fifteenth example of the invention.
Figure 27B:
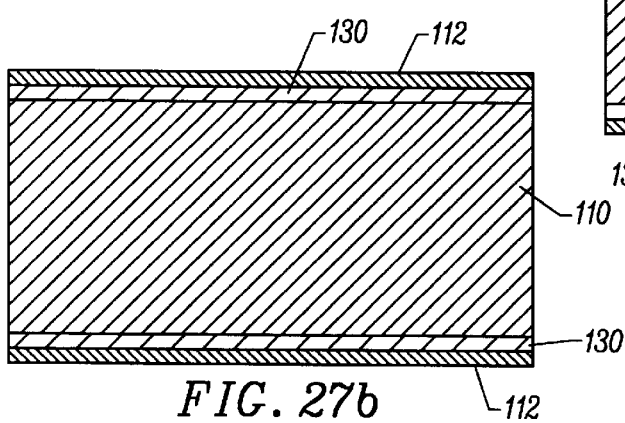

A single crystal (100) silicon wafer approximately 500 μm thick is used as a starting wafer 110, as shown in FIG. 27(a). The wafer is cleaned (step A) and approximately 0.8 μm of phosphosilicate glass (PSG) is deposited (step E). The PSG is then densified (step G). Then, 0.5 μm of silicon nitride (step D) is deposited. The deposited silicon nitride 112 and PSG 130 is shown in FIG. 27(b). The silicon nitride is used as the masking material for the silicon isotropic etch.

Figure 27C:
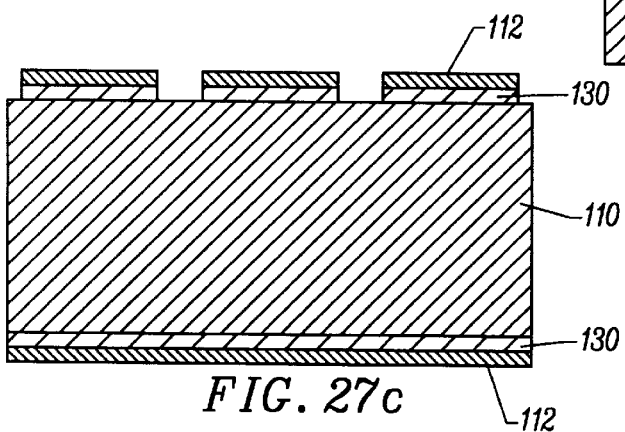
Figure 27D:
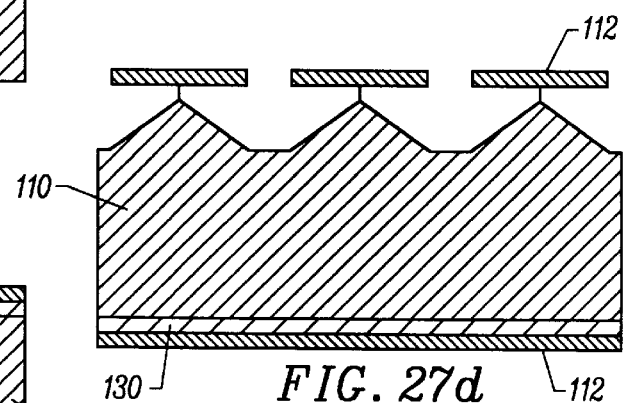
Figure 27E:
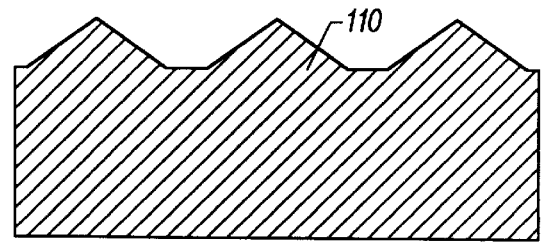

The silicon nitride is then patterned (step H). Afterwards, the silicon nitride and oxide layer is etched (step L), and the resist is stripped (step K), producing the device of FIG. 27(c). The wafer is then submerged in an isotropic silicon etchant (step O). This processing results in the device of FIG. 27(d). Afterwards, the wafer is submerged in HF (step S) to remove the silicon nitride and PSG. Finally, the wafer is rinsed in deionized water for approximately 15 minutes, producing the device shown in FIG. 27(e).

All of the foregoing examples share the common trait that they result in a device with an isotropically etched tip. The advantage of the disclosed probes over standard stainless steel probes is that they can be made with smaller cross-sections, sharper tips, and can include integrated circuitry or micromachined structures. Small cross-sections and sharper tips result in minimized pain and tissue damage and the integrated circuitry provides a convenient means to incorporate sensing, stimulating, pumping, and valving operations. Unlike prior art probes, the probes of the present invention are constructed without expensive Boron doping. Further, the processing does not require the use of the dangerous carcinogen ethylenediamine pyrocatechol.

Many process variations have been described to result in a variety of shaft cross-sections. In addition, several styles of substrates have been disclosed, including silicon on insulator, thinner than standard silicon wafers, and standard thickness silicon wafers. However, all of the probe variations maintain the desired, high tip sharpness, which results from the isotropic etch.

Although single crystal silicon is the preferred fabrication material, other materials may be utilized, including, but not limited to, stainless steel, aluminum, and titanium. Typically, these materials are not used in their single crystal form so they cannot be used in process flows relying upon highly anisotropic properties.

The silicon probes of the invention may be coated with nickel, titanium, gold, or similar metals which are either sputtered or plated to improve the strength or surface characteristics of the probes. An organic coating, such as Parylene, may also be used for strength enhancement. The probes of the invention may also be thermally oxidized to improve their strength or surface characteristics. Other process variations include the use of an inductively coupled plasma etch to make the vertical side walls of the probe, as shown in FIGS. 6 and 7.

The foregoing description, for purposes of explanation, used specific nomenclature to provide a thorough understanding of the invention. However, it will be apparent to one skilled in the art that the specific details are not required in order to practice the invention. In other instances, well known circuits and devices are shown in block diagram form in order to avoid unnecessary distraction from the underlying invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following Claims and their equivalents.

What is claimed is:

1. A method of fabricating an epidermal abrasion device, said method comprising the steps of:

providing a semiconductor substrate with a planar surface:

defining a mask configuration on said semiconductor substrate to facilitate the formation of an epidermal abrasion device; and exposing said mask configuration on said semiconductor substrate to an isotropic etchant, said isotropic etchant forming a matrix of isotropically etched structures on said semiconductor substrate adapted for epidermal abrasion, said isotropically etched structures having isotropically etched sidewalls positioned between wide bases and narrow tips;

wherein said exposing step includes forming a matrix of isotropically etched pyramids on said semiconductor substrate.

2. The method of claim 1 further comprising the step of using a phosphosilicate glass layer to facilitate formation of said matrix of isotropically etched pyramids on said semiconductor substrate.

3. The method of claim 1 wherein each said structure has a vertical height of between 20 μm and 350 μm.

4. The method of claim 1 wherein horizontal spacing between tops of adjacent ones of said isotropically etched structures is greater than two times the vertical height of each adjacent structure.

5. The method of claim 1 wherein said providing step includes providing a silicon on-insulator (SOI) wafer as said semiconductor substrate.

6. The method of claim 1 wherein said exposing step is performed without the use of ethylenediamine pyrocatechol.

7. A method of fabricating an epidermal abrasion device, said method comprising the steps of:

providing a semiconductor substrate with a planar surface;

defining a mask configuration on said semiconductor substrate to facilitate the formation of an epidemial abrasion device; and exposing said mask configuration on said semiconductor substrate to an isotropic etchant, said isotropic etchant forming a matrix of isotropically etched structures on said semiconductor substrate adapted for epidermal abrasion, said isotropically etched structures having isotropically etched sidewalls positioned between wide bases and narrow tips; wherein said exposing step includes exposing said mask configuration on said semiconductor substrate to an isotropic etchant to form said matrix of isotropically etched structures in which each structure has a vertical height of at least 20 $\mu$m.

8. The method of claim 7 wherein each said structure has a vertical height of between 20 $\mu$m and 350 $\mu$m.

9. The method of claim 8 wherein horizontal spacing between tops of adjacent ones of said isotropically etched structures is greater than two times the vertical height of each adjacent structure.

10. The method of claim 8 wherein said providing step includes the step of providing a silicon on-insulator (SOI) wafer as said semiconductor substrate.

11. The method of claim 8 wherein said exposing step is performed without the use of ethylenediamine pyrocatechol.

* * * * *